United States Patent [19]
Bannai et al.

[11] Patent Number: 5,364,883
[45] Date of Patent: Nov. 15, 1994

[54] ISOCARBOCYCLINS FOR THE TREATMENT OF LIVER AND KIDNEY DISEASES

[75] Inventors: Kiyoshi Bannai; Toshio Tanaka; Yoshinori Kato, all of Hino; Tamotsu Koyama, Hachioji; Satoshi Asano, Hino; Akira Ohtsu, Oume; Seizi Kurozumi, Kokubunji; Makoto Ogawa; Yoshio Mori, both of Chiba, all of Japan

[73] Assignee: Teijin Limited, Osaka, Japan

[21] Appl. No.: 55,787

[22] Filed: May 3, 1993

Related U.S. Application Data

[63] Continuation of Ser. No. 571,542, Aug. 22, 1990, abandoned.

[30] Foreign Application Priority Data

Dec. 23, 1988 [JP] Japan ................. 63-323687

[51] Int. Cl.⁵ .......................................... A61K 31/557
[52] U.S. Cl. ............................................. 514/530
[58] Field of Search ............................. 514/530

[56] References Cited

U.S. PATENT DOCUMENTS 4,788,319  11/1988  Hazato .................. 560/11

FOREIGN PATENT DOCUMENTS

| | | | |
|---|---|---|---|
| 216585 | 4/1987 | European Pat. Off. | C07C 177/00 |
| 247740 | 12/1987 | European Pat. Off. | A61K 31/55 |
| 62-19565 | 1/1987 | Japan | A61K 31/557 |
| 62-132839 | 6/1987 | Japan | C07C 59/125 |
| 62-138448 | 6/1987 | Japan | C07C 51/367 |
| 63-152319 | 6/1988 | Japan | A61K 31/55 |
| 000020 | 1/1989 | Japan | A61K 31/557 |
| WO-A-8600808 | 2/1986 | WIPO | |

OTHER PUBLICATIONS

Chemical Abstracts 109(1):6304.
Chemical Abstracts 106(23):196121.
Park, I. Y. et al, K'at'ollik Taehak Uihakpu Nonmunjip 38(1):141–50 1985.
Teijin Ltd., Patent Abstracts of Japan, vol. 11, No. 24 (C-399-[2471] 23 Jan. 1987 JP-A-61197518.

*Primary Examiner*—Marianne M. Cintins
*Assistant Examiner*—William R. A. Jarvis
*Attorney, Agent, or Firm*—Wenderoth, Lind & Ponack

[57] ABSTRACT

16(S)-Isocarbacyclins have been found to the useful in the treatment of liver and kidney diseases.

10 Claims, No Drawings

ISOCARBOCYCLINS FOR THE TREATMENT OF LIVER AND KIDNEY DISEASES

This application is a continuation of now abandoned application Ser. No. 07/571,542, field Aug. 22, 1990.

INDUSTRIAL USE FIELD

The present invention relates to a use of isocarbacyclins in the prevention or therapy of organ disorders, a pharmaceutical composition containing the same and a process for its production.

CONVENTIONAL ARTS

Prostaglandins (hereinafter sometimes abbreviated as PG) have various physiological actions such as a strong platelet aggregation inhibitory action, an anti-hypertensive action, an action to inhibit the secretion of gastric acid, a contractive action of smooth muscles, a diuretic action, etc. They are substances useful for the therapy or the prevention of peripheral circulatory disorders, cardiac infarction, angina, arteriosclerosis, hypertension, gastric ulcer, duodenal ulcer, induction of labor, artificial termination of pregnancy and the like.

Recently it has been brought to light that some kind of these prostaglandins have an action of protecting cells of an endogeneous tissue, a so-called cell protecting action. This cell protecting action is present in all endogeneous cells. It is said that for example, a therapeutic effect on the gastric ulcer, a focal contraction effect of cardiac infarction, a preventive effect of the lung injury involved by an endotoxin shock and the like are attributable to this cell protecting action [see "Igaku no ayumi (a step in medical science), a Japanese material, vol. 125, p.p. 250, 1983]. Further, it is known that prostaglandins exhibit a cell protecting action to hepatocells. For instance, it is reported that 16,16-dimethyl-$PGE_2$, a structural modifier of $PGE_2$, is useful to prevent the necrosis of parenchymal liver cells of rats induced by carbon tetrachloride and galactosamine [see "Folia Histochemi et Cytochemica" vol. 18, p.p. 311, 1980; and "Gastroenterology", vol.81, p.p. 211, 1981]. Further, regarding an action to protect hepatocytes produced by $PGE_2$ and its structural modifier (15-methyl-$PGE_2$, 16,16-dimethyl-$PGE_2$, etc.) this is mentioned in U.S. Pat. No. 4,374,856. Further, we discovered that thia-$PGE_1$s would have an inhibitory action of hepatic disorders and filed an application separately (Japanese Laid-Open Patent Publn. No. 62-129218). Moreover, the following action is reported in Japanese Laid-Open Patent Publns. Nos. 58-164512, 58-203911 and 62-277352, i.e. a cell protecting action exhibited by a structural modifier of 6-oxo-$PGE_1$.

Additionally, it is reported that prostacyclins ($PGI_2$) have an action of protecting a cat's hepatic tissue under an oxgen scarce condition [see "Amer. J. Physiol. vol. 238, p.p. 176, 1980]. We discovered that 7-fluoro-$PGI_2$s, a derivative for prostacyclins, would have an inhibitory action of hepatic disorders and filed an application separately (Japanese Laid-Open Patent Publn. No. 63-27433). Furthermore, it is reported that 6,9-alpha-nitrilo-$PGI_1$ also have a hepatic tissue protecting action (see official gazettes of Japanese Laid-Open Patent Publns. No. 58-164512 and 58-203911). And besides, it is reported that iloprost, a carbacyclin derivative, and nileprost, of cyanoprostacyclins, also have an action of protecting a liver, a pancreas and a kidney (see an official gazette of Japanese Announcement No. 61-502819).

Further, in recent years prostaglandins have been utilized in the field of organ transplantation, thanks to its strong cell protecting action (see "Modern medical science" written by K. Ohta, No. 18, p.p. 2693–2697, 1986). Namely, prostaglandins are used for storing any organ enucleated from a donor to insure the protection of said organ at the time of its transplantation, minimizing any trouble occurring until the transplantation operation and to ensure the preservation of said organ in a good condition. For instance, it is reported that natural prostacyclins ($PGI_2$) are useful for the preservation of a liver and a kidney (M. Monden et al., Ann. Surg. vol. 196 p.p. 38, 1982, J. W. Bradlet et al., Transplan. Proc., vol. 15, p.p. 424, 1983). There are also reports that OP-41483, a derivative for prostacyclin, is useful for the storage of a kidney (M. Tobimatsu et al, Transplant. Proc., vol. 17 p.p. 1461, 1985) and that prostaglandins are useful to inhibit the rejection at the time of organ transplantation by virtue of its strong cell protecting action ("Modern medical science" written by K. Ohta, No. 18, p.p. 2693–2697, 1986). We discovered that isocarbacyclins of the following formula (I)-a had a protecting action at the time of enucleating such organs from a living human body and filed an application separately (see an official gazette of Japanese Laid-Open Patent Publn. No. 64–20).

By the way, naturally occurring prostacyclins are a local hormone produced in vivo mainly on endothelium of an arteria and an attempt has been made of providing this as a drug directly by utilizing being an important factor which regulates the cell function in vivo depending on its strong physiological activity such as a platelet aggregation inhibitory activity, a vasodilator activity and the like ["Clinical Pharmacology of Prostacyclin" written by P. J. Lewis, J. O. Grady et al, Raven Press, N.Y. 1981]. However, since naturally ocurring prostacyclins have an enol ether bond which is very easy to hydrolyze within the molecule, they are easily deactivated under neutral or acidic conditions and therefore, cannot be said to be a desirable compound because of being chemically unstable as medicines. Thus, ardent studies have been made of chemically stable synthetic prostacyclin derivatives which have the same physiological activity as that of naturally ocurring prostacyclin [see "Synthesis", 1984, p.p. 449]. As a result, the Inventors were successful in the synthesis of 9(O)-methano-$\Delta^{6(9\alpha)}$-orostaglandins $I_1$ (isocarbacyclins), prostacyclins of the following formula (I)-a which fully satisfy chemically stable properties by replacing an oxygen atom in the 6,9 alpha-position of prostacyclin with a methine group (—CH=)(see official gazettes of European Patent Laid-Open Publns. Nos. 216585 and 247740 and U.S. Pat. No. 4,788,319).

Among these isocarbacyclins of the formula (I)-a derivatives wherein n=0, in particular, had strong physiological actions such as a platelet aggregation inhibitory action, an antihypertensive action, etc. equal to those of naturally occurring prostacyclins and were useful as a pharmaceutical agent for circulatory organs. Moreover, these isocarbacyclins were useful as an agent for lowering the lipid in blood (see Japanese Laid-Open Patent Publn. No. 63-152319).

While, in the official gazette of Japanese Laid-Open Patent Publn. No. 62-19565 are disclosed 15- or 16-hydroxy-3-thia (iso)carbacyclins and a process for their preparation. It is also disclosed that they have a platelet aggregation inhibitory activity.

Further, regarding 15-hydroxy-3-oxa(iso)carbacyclins, there is disclosed a process for the identification of these compounds and a process for their preparation in the official gazette of Japanese Laid-Open Patent Publn. No. 2-138448. And concerning 16-hydroxy 3-oxa(iso)-carbacyclins, there is disclosed a process for the identification of these compounds and a process for their preparation in the official gazette of Japanese Laid-Open Patent Publn. No. 2-138448.

DISCLOSURE OF THE INVENTION

Consequently, an object of this invention is to provide a process for using particular isocarbacyclins in the prevention or therapy of organ disorders as well as pharmaceutical compositions containing the same. Another object of the invention is to provide the above process and pharmaceutical compositions on the basis of such discovery that specific isocarbacyclins are excellent in the action to prevent or cure organ disorders in vivo and moreover, they are low in the action on the circulatory system such as an antihypertensive action or a platelet aggregation inhibitory action and consequently, the aimed actional selectivity is high.

A further object of the invention is to provide a process for the prevention or therapy of disorders of organs in vivo, especially a liver or a kidney by using isocarbacyclins which are specially excellent in the action for preventing or curing the above disorders and is to provide pharmaceutical compositions containing the same. A still further object of the invention is to provide the use of isocarbacyclins in the preparation of pharmaceutical compositions which are useful for the above prevention or therapy of organ disorders.

Additional other objects and merits of the invention will be apparent from the following explanation.

According to the present invention, the above objects and advantages firstly lie in the provision of pharmaceutical compositions useful for the prevention or therapy of organ disorders which contain isocarbacyclins of the following formula (I→a:

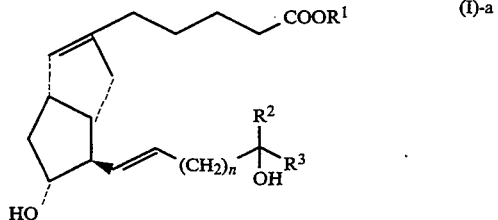

(I)-a wherein $R^1$ denotes a hydrogen atom, a $C_1-C_{10}$ alkyl group, a group —$CH_2COOR^{11}$ in which $R^{11}$ is a hydrogen atom or a $C_1-C_{10}$ alkyl group or one equivalent of cation; $R^2$ denotes a hydrogen atom or a methyl group; $R^3$ denotes a straight chain or branched chain $C_3-C_{10}$ alkyl group, a straight chain or branched chain $C_3-C_6$ alkyl group substituted by an optionally substituted phenyl group, phenoxy group or a $C_3-C_{10}$ cycloalkyl group, a straight chain or branched chain $C_3-C_{10}$ alkenyl group, a straight chain or branched chain $C_3-C_{10}$ alkynyl group, an optionally substituted $C_3-C_{10}$ cycloalkyl group, an optionally substituted phenyl group or an optionally substituted phenoxy group; n is 0 or 1; and substituents for the above optionally substituted groups are a halogen atom, a hydroxyl group, a $C_2-C_7$ acyloxy group, a $C_1-C_6$ alkyl group optionally substituted by a halogen atom, a $C_1-C_4$ alkoxy group optionally substituted by a halogen atom, a nitrile group, a carboxyl group or a $C_1-C_6$ alkoxy carbonyl group, and/or enantiomers thereof as active ingredients together with pharmaceutically acceptable carriers or adjuvants.

In the above formula (I→a $R^1$ signifies a hydrogen atom, a $C_1-C_{10}$ alkyl group, a group —$CH_2COOR^{11}$ wherein $R^{11}$ is a hydrogen atom or a $C_1-C_{10}$ alkyl group or one equivalent of cation. Examples of the $C_1-C_{10}$ alkyl group expressed by $R^1$ and $R^{11}$ may independently include straight chain or branched chain types such as methyl, ethyl, n-propyl, iso-propyl, n-butyl, sec-butyl, tert-butyl, n-pentyl, n-hexyl, n-heptyl, n-octyl, n-nonyl, n-decyl, etc. As one equivalent of cation can be given, for example, an alkali metal cation like $Na^+$ or $K^+$, a divalent or trivalent metal cation like ½ $Ca^{2+}$, ½ $Mg^{2+}$ or ⅓ $Al^{3+}$, an ammonium cation like ammonium ion or tetramethyl ammonium ion, etc. As $R^1$ is especially preferably a hydrogen atom, a methyl group, a t-butyl group or a carboxymethyl group.

In the above formula (I→a $R^2$ signifies a hydrogen atom or a methyl group. Especially where n=0 a hydrogen atom is preferable, and a methyl group is preferred where n=1.

In the above formula (I→a $R^3$ stands for a straight chain or branched chain $C_3-C_{10}$ alkyl group, a straight chain or a branched chain $C_1-C_6$ alkyl group which is substituted by an optionally substituted phenyl group, an optionally substituted phenoxy group or an optionally substituted $C_3-C_{10}$ cycloalkyl group; a straight chain or branched chain $C_3-C_{10}$ alkenyl group; a straight chain or branched chain $C_3-C_{10}$ alkynyl group; an optionally substituted $C_3-C_{10}$ cycloalkyl group; an optionally substituted phenyl group; or an optionally substituted phenoxy group.

Examples of the straight chain or branched chain $C_3-C_{10}$ alkyl group may include n-propyl, n-hexyl, n-pentyl, n-heptyl, n-octyl, n-decyl, 1-methylpentyl, 1-methylhexyl, 1,1-dimethylpentyl, 2-methylpentyl, 2-methylhexyl, 5-methylhexyl or 2,5-dimethylhexyl group. Preferably this is n-butyl, n-pentyl, n-hexyl, (R)- or (S)- or (RS)-1-methylpentyl, (R)- or (S)- or (RS)-2-methylhexyl group.

As the substituted straight chain or branched chain $C_1-C_6$ alkyl group can be given a substituted alkyl group containing 1 to 6 carbon atoms among the above exemplified alkyl groups. Such substituent is an optionally substituted phenyl group, an optionally substituted phenoxy group or an optionally substituted $C_3-C_{10}$ cycloalkyl group. Subtituents for the optionally substituted phenyl group, optionally substituted phenoxy group and optionally substituted $C_3-C_{10}$ cycloalkyl group are a halogen atom, a hydroxyl group, a $C_2-C_7$ acyloxy group, a $C_1-C_6$ alkyl group optionally substituted by a halogen atom, a $C_1-C_4$ alkoxy group optionally substituted by a halogen atom, a nitrile group, a carboxyl group or a $C_1-C_6$ alkoxy carbonyl group.

Examples of the halogen atom as the above substituent includes fluorine, chlorine and bromine. In particular, fluorine or chlorine is desirable. Examples of the $C_2-C_7$ acyloxy group may include acetoxy, propionyloxy, n-butyryloxy, iso-butyryloxy, n-valeryloxy, iso-valeryloxy, caproyloxy, enanthyloxy or benzoyloxy. Preferable examples of the $C_1-C_4$ alkyl group optionally substituted by halogen may include methyl, ethyl, n-propyl, iso-propyl, n-butyl, chloromethyl, dichloromethyl, trifluoromethyl, etc. Preferable examples of the $C_1$–$C_4$ alkoxy group optionally substituted by halogen may include methoxy, ethoxy, n-propoxy, iso-propoxy, n-butoxy, chloromethoxy, dichloromethoxy, trifluoromethoxy, etc. And as the ($C_1$–$C_6$) alkoxy carbonyl group can be given, for example, methoxycarbonyl, ethoxycarbonyl, butoxycarbonyl, hexylcarbonyl, etc.

Thus, examples of the above optionally substituted $C_3$–$C_{10}$ cycloalkyl group may include cyclopropyl, cyclobutyl, cyclopentyl, cyclohexyl, cycloheptyl, cyclooctyl, ($C_1$–$C_6$)alkyl cyclopentyl, ($C_1$–$C_4$)alkylcyclohexyl, dimethylcyclopentyl, dimethylcyclohexyl, chlorocyclopentyl, bromocyclohexyl, iodocyclopentyl, fluorocyclohexyl group, etc. Preferably, the cyclopentyl group and the cyclohexyl group.

Further, examples of the $C_3$–$C_{10}$ alkenyl group expressed by $R^3$ may include 2-butenyl, 2-pentenyl, 3-pentenyl, 2-hexenyl, 4-hexenyl, 2-methyl-4-hexenyl, 2,6-dimethyl-5-heptenyl group, etc.

As the $C_3$–$C_{10}$ alkynyl group can be given 2-butynyl, 2-pentynyl, 3-pentynyl, 2-hexynyl, 4-hexynyl, 2-octynyl, 5-decynyl, 1-methyl-3-pentynyl, 1-methyl-3-hexynyl, 2-methyl-4-hexynyl group, etc.

Moreover, as the optionally substituted phenyl group, optionally substituted phenoxy group or optionally substituted $C_3$–$C_{10}$ cycloalkyl group which is expressed by $R^3$ can be given, for example, the same type as those exemplified as the subtituent for the above substituted $C_1$–$C_6$ alkyl group.

As $R^3$ above all, n-butyl, n-pentyl, 1-methylpentyl, 2-methylhexyl, cyclopentyl, cyclohexyl, 2,6-dimethyl-5-heptenyl, 1-methyl-3-pentenyl and 1-methyl-3-hexynyl are preferable among the above groups. In the above formula (I→a n is 0 or 1.

In the case of isocarbacyclins expressed by the above formula (I→a the carbon atom to which $R^2$, $R^3$ and OH are linked is put in an environment of asymmetric carbon atom. Optical isomers are present therein. If this is explained by giving the case of n=0 as an example, both compounds of the following isocarbacyclins come to exist, i.e. isocarbacyclins having a natural type stereo configuration in the 15-position expressed by the formula [I-1]:

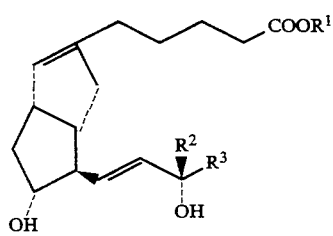

wherein $R^1$, $R^2$ and $R^3$ have the above definitions, and isocarbacyclins having a non-natural type stereo configuration in the 15-position expressed by the formula [I-2]:

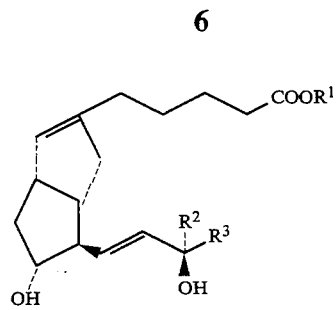

wherein $R^1$, $R^2$ and $R^3$ have the above definitions.

The use application of this patent covers any one of these compounds or a mixture of these compounds in an optional proportion. Especially when $R^2$ is a hydrogen atom, isocarbacyclins expressed by the above formula [I-1] are preferable. The same also applies to the case of n=1 and the use application covers (R)-configuration and (S)-configuration at the 16 position and a mixture thereof in any optional proportion. However, the compound having (S)-configuration is more desirable.

Since stereo configurations in 8-, 9-, 11- and 12 positions of prostacyclins expressed by the above formula (1→a are the same as those of naturally occurring prostaglandins I2, isomers are especially steric ones. Thus, the present invention includes steric isomers depending on the difference of stereo configurations in respective positions or a mixture thereof having an optional proportion.

According to the present invention, there are provided a pharmaceutical composition useful for the prevention or therapy of organ disorders which contains 4-heteroisocarbacyclins of the following formula (I→b, an analogous substance of isocarbacyclins expressed by the above formula (I→a:

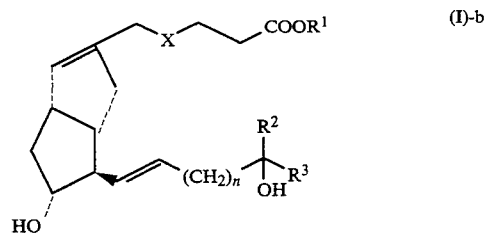

wherein X denotes an oxygen atom or a sulfur atom; $R^1$, $R^2$ and $R^3$ and n have the same definitions as above, and/or enantiomers thereof as active ingredients together with pharmaceutically acceptable carriers or adjuvants and a pharmaceutical composition useful for the prevention or therapy of organ disorders which contains 3-heteroisocarbacyclins of the following formula (I→c:

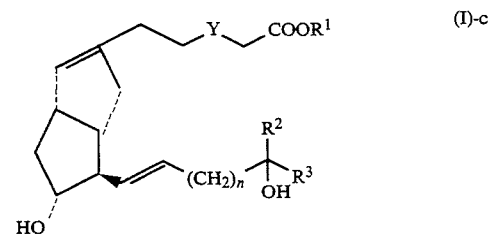

wherein Y denotes an oxygen atom or a sulfur atom;
$R^1$, $R^2$ and $R^3$ and n have the same definitions as above, and/or enantiomers thereof as active ingredients together with pharmacologically acceptable carriers or adjuvants.

The definitions of $R^1$, $R^2$, $R^3$ and n in the above formulae (I→b and (I→c are the same as those in the above formula (I→a. X in formula (I→b and Y in (I→c are both an oxygen atom or a sulfur atom.

As isocarbacyclins of the present invention represented by the above formulae (I→a, (I ) b and (I→c can be exemplified the following compounds, for instance:

(1) 9(O) methano-$\Delta^{6(9\alpha)}$-prostaglandin $I_1$(isocarbacyclin)
(2) 20-methyl-9(O)-methano-$\Delta^{6(9\alpha)}$-prostaglandin $I_1$
(3) 16-methyl-9(O)-methano-$\Delta^{6(9\alpha)}$-prostaglandin $I_1$
(4) 16,16-dimethyl-9(O)-methano-$\Delta^{6(9\alpha)}$-prostaglandin $I_1$
(5) 17-methyl-9(O)-methano-$\Delta^{6(9\alpha)}$-prostaglandin $I_1$
(6) 17,20-dimethyl-9(O)-methano-$\Delta^{6(9\alpha)}$-prostaglandin $I_1$
(7) (17R)-isomer of (6)
(8) (17S)-isomer of (6)
(9) 15-methyl-9(O)-methano-$\Delta^{6(9\alpha)}$-prostaglandin $I_1$
(10) 17,18-dehydro-9(O)-methano-$\Delta^{6(9\alpha)}$-prostaglandin $I_1$
(11) 20-isopropylidene-17-methyl-9(O)-methano-$\Delta^{6(9\alpha)}$-prostaglandin $I_1$
(12) 18,18,19,19-tetradehydro-16-methyl-9(O)-methano-$\Delta^{6(9\alpha)}$-prostaglandin $I_1$
(13) 18,18,19,19-tetradehydro-16,20-dimethyl-9(O)-methano-$\Delta^{6(9\alpha)}$-prostaglandin $I_1$
(14) (16S)-isomers of (3), (12) and (13)
(15) (16R)-isomers of (3), (12) and (13)
(16) 16,17,18,19,20-pentanor-15-cyclopentyl-9(O)-methano-$\Delta^{6(9\alpha)}$-prostaglandin $I_1$
(17) 16,17,18,19,20-pentanor-15-cyclohexyl-9(O)-methano-$\Delta^{6(9\alpha)}$-prostaglandin $I_1$
(18) 17,18,19,20-tetranor-16-(p-fluorophenoxy)-9(O)-methano-$\Delta^{6(9\alpha)}$-prostaglandin $I_1$
(19) 17,18,19,20-tetranor-16-cyclohexyl-9(O)-methano-$\Delta^{6(9\alpha)}$-prostaglandin $I_1$
(20) 15-deoxy-16-hydroxy-9(O)-methano-$\Delta^{6(9\alpha)}$-prostaglandin $I_1$
(21) 15-deoxy-16-hydroxy-16-methyl-9(O)-methano-$\Delta^{6(9\alpha)}$-prostaglandin $I_1$
(22) (16S)-isomer of compound (21)
(23) (16R)-isomer of compound (21)
(24) (16S)-15-deoxy-16-hydroxy-16-methyl-9(O)-methano-$\Delta^{6(9\alpha)}$-4-oxaprostaglandin $I_1$
(b 25) (16S)-15-deoxy-16-hydroxy-16-methyl-9(O)-methano-$\Delta^{6(9\alpha)}$-4-thiaprostaglandin $I_1$
(26) (16S)-15-deoxy-16-hydroxy-16-methyl-9(O)-methano-$\Delta^{6(9\alpha)}$-3-thiaprostaglandin $I_1$
(27) (16)-15-deoxy-16-hydroxy-16-methyl9(O)-methano-$\Delta^{6(9\alpha)}$-3-oxaprostaglandin $I_1$
(28) Methyl esters of compounds (1) to (27)
(29) Ethyl esters of compounds (1) to (27)
(30) t-butyl esters of compounds (1) to (27)
(31) Carboxymethyl esters of compounds (1) to (27)
(32) Sodium salts of compounds (1) to (27)
(33) Potassium salts of compounds (1) to (27)
(34) Ammonium salts of compounds (1) to (27)
(35) Enantiomers of compounds (1) to (34)
(36) Steric isomers in 8-, 9-, 11-, 12- and 15-positions of compounds (1) to (34)

However, the present invention will not be restricted by these compounds.

Shown below are physical values of several typical compounds inclusive within the formula (I→a among the above compounds. Physical values of the compounds of formulae (I→b and (I→c were shown in referential examples below. Further, numbers in parenthesis indicate the above compounds.

(1) 9(O)-methano-$\Delta^{6(9\alpha)}$-prostaglandin $I_1$ (isocarbacyclin)

NMR (CDCl$_3$, $\gamma$ ppm) 0.88 (3H, t, J=6 Hz ), 2.98 (1H, m), 3.73 (1H, q, J=8 Hz ), 4.02 (1H, q, J=7 Hz), 5.28 (1H, bs), 5.48 (2H, m), 5.3–5.9 (3H, br; disappeared in D$_2$O) IR (liquid film, cm$^{-1}$), 3400, 3100–2400, 1700, 1085, 965. Mass (m/e) 332, 314, 288.

(3) 16-methyl-9(O)-methano-$\Delta^{6(9\alpha)}$-prostaglandin $I_1$

NMR (CDCl$_3$, $\gamma$ ppm) 0.7–1.1 (6H, m), 2.7–3.3 (1H, br), 3.5–4.3 (2H, br), 5.0–5.3 (3H, br; disappeared in D$_2$O) 5.30 (1H, bs), 5.48 (2H, m) IR (liquid film, cm$^{-1}$), 3350, 3400–2400, 1705, 1085, 995, 065.

(8) (17S)-17,20-dimethyl-9(O)-methano$\Delta^{6(9\alpha)}$-prostaglandin $I_1$

NMR (CDCl$_3$, $\gamma$ ppm) 0.88 (6H, m), 2.98 (1H, br), 3.75 (1H, q, J=8 Hz), 4.13 (1H, q, J=7 Hz), 5.29 (1H, bs), 5,47 (1H, dd, J=15H, 8 Hz), 5.50 (1H, dd, J=15H, 8 Hz), 5.95 (3H, br; disappeared in D$_2$O) IR (liquid film, cm$^{-1}$), 3350, 3400–2400, 1712, 1085, 995, 968. Mass (m/e) 360 (M-H$_2$O), 342, 316.

(16) 16,17,18,19,20-pentanor-15-cyclopentyl-9(O)-methano-$\Delta^{6(9\alpha)}$-prostaglandin $I_1$ NMR (CDCl$_3$, $\gamma$ ppm) 2.7–3.2 (1H, br), 3.5–4.0 (2H, m), 5.0–5.3 (4H, br; 3H disappeared in D$_2$O) IR (liquid film, cm$^{-1}$), 3350, 3400–2400, 1705, 1085, 995, 965.

(17) 16,17,18,19,20-pentanor-15-cyclohexyl-9(O)-methano-$\Delta^{6(9\alpha)}$-prostaglandin $I_1$ NMR (CDCl$_3$, $\gamma$ ppm) 2.7–3.2 (1H, br), 3.5–4.0 (2H, m), 5.0–5.3 (3H, br; disappeared in D$_2$O), 5.29 (1H, br), 5.3–5.55 (2H, m), 5.95 (3H, br); disappeared in D$_2$O) IR (liquid film, cm$^{-1}$), 3350, 3100–2400, 1708, 1085, 965.

(21) 15-deoxy-16-hydroxy-16-methyl-9(O)-methano-$\Delta^{6(9\alpha)}$-prostaglandin $I_1$ NMR (CDCl$_3$, $\gamma$ ppm) 0.88 (3H, t, J=6 Hz), 1.16 (3H, s), 2.65–3.2 (1H, m), 3.5–3.9 (1H, m), 4.6–5.2 (3H, br; disappeared in D$_2$O), 5.26 (1H, bs), 5.25–5.55 (2H, m). IR (liquid film, cm$^{-1}$), 3350, 3100–2400, 1705, 965. Mass (m/e) 326, 329, 328, 302, 246.

(22)-1 . . . (16S) -isomer of (21)

NMR (CDCl$_3$, $\gamma$ ppm) 0.88 (3H, t, J=6 Hz), 1.16 (3H, s), 2.65–3.2 (1H, m), 3.5–3.9 (1H, m), 4.6–5.2 (3H, br; disappeared in D$_2$O), 5.26 (1H, bs), 5.25–5.55 (2H, m). IR (liquid film, cm$^{-1}$), 3350, 3100–2400, 1705, 965. Mass (m/e) 346, 329, 328, 302, 246.

(23)-1 . . . (16R)-isomer of (21)

NMR (CDCl$_3$, $\gamma$ ppm) 0.88 (3H, t, J=6 Hz), 1.16 (3H, s), 2.65–3.2 (1H, m), 3.5–3.9 (1H, m), 4.6–5.2 (3H, br; disappeared in D$_2$O) 5.28 (1H, bs), 5.25–5.55 (2H, m). IR (liquid film, cm$^{-1}$), 3350, 3100–2400, 1705, 965. Mass (m/e) 346, 329, 328, 302, 246.

(24)-1 . . . Methyl ester of (1)

NMR (CDCl$_3$, $\gamma$ ppm) 0.88 (3H, t, J=6 Hz), 2.99 (1H, m), 3.676 (3H,s), 3.75 (1H, q, J=8 Hz), 4.06 (1H, q, J=7 Hz), 5.28 (1H, bs), 5.53 (2H, m). IR (liquid film, cm$^{-1}$), 3360, 1740, 1090, 965. Mass (m/e) 362, 328, 302.

(24)-2 ... Methyl ester of (8)

NMR (CDCl$_3$, γ ppm) 0.88 (6H, m), 2.98 (1H, m), 3.67 (3H, s), 3.75 (1H, m), 4.12 (1H, m), 5.9 (1H, bs), 5.48 (2H, m). IR (liquid film, cm$^{-1}$), 3380, 1740, 966.

(24)-3 ... Methyl ester of (16)

NMR (CDCl$_3$, γ ppm) 2.7-3.2 (1H, br), 3.5-4.0 (2H, m), 3.67 (3H, s), 5.28 (1H, bs), 5.49 (2H, m). IR (liquid film, cm$^{-1}$), 3400, 1742, 968.

(24)-4 ... Methyl ester of (21)

NMR (CDCl$_3$, γ ppm) 0.88 (3H, t, J=6 Hz), 1.16 (3H, s), 2.7-3.2 (1H, m), 3.5-3.9 (1H, m), 3.66 (3H, s), 5.28 (1H, bs), 5.2-5.6 (2H, m). IR (liquid film, cm$^{-1}$), 3400, 1740, 968. (24) -5 ... Methyl ester of (22)-1

NMR (CDCl$_3$, γ ppm) 0.88 (3H, t, J=6 Hz), 1.16 (3H, s), 2.7-3.2 (1H, br), 3.5-3.9 (1H, m), 3.67 (3H, s), 5.28 (1H, bs), 5.2-5.6 (2H, m). IR (liquid film, cm$^{-1}$), 3400, 1740, 968.

(24)-6 ... Methyl ester of (23)-1

NMR (CDCl$_3$, γ ppm) 0.88 (3H, t, J=6 Hz), 1.16 (3H, s), 2.7-3.2 (1H, br), 3.5-3.9 (1H, m), 3.67 (3H, s), 5.27 (1H, bs), 5.5-5.6 (2H, m). IR (liquid film, cm$^{-1}$) 3400, 1740, 968.

Prostacyclins I$_1$ (isocarbacyclin) represented by the above formula (I→a are easily produced in the known way. For instance, the compounds of formula (I→a can be produced by the process as mentioned in each of European Patent Laid-Open Nos. 216585 and 247740 and U.S. Pat. No. 4788319 corres. to the latter.

Further, 4-heteroisocarbacyclins expressed by the above formula (I→b can be produced according to the following reaction scheme 1. Moreover, 3-heteroisocarbacyclins of the above formula (I→c can be produced in accordance with the following reaction scheme 2. In these reaction schemes the reaction at each step per se is known. The details of the reaction in each step will be apparent from the following referential examples.

Reaction Scheme 1

Process for the production of 4-heteroisocarbacyclins

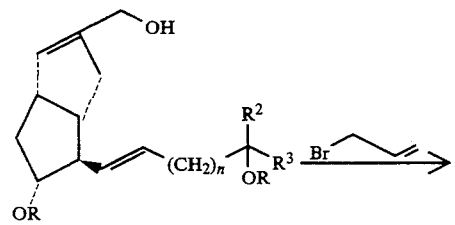

in which R represents a protective group of the hydroxy group.

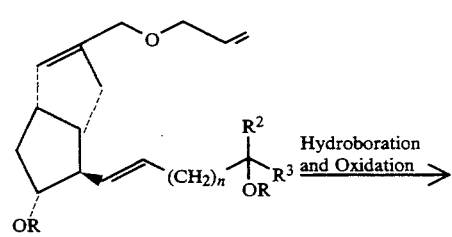

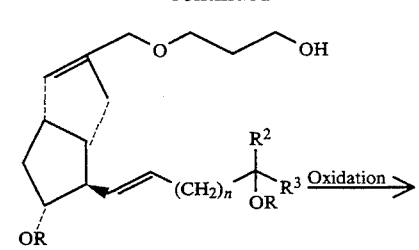

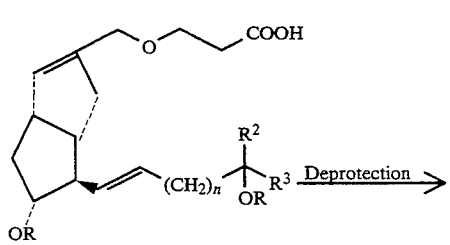

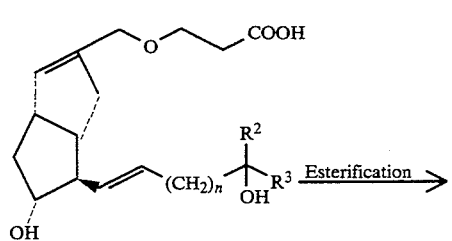

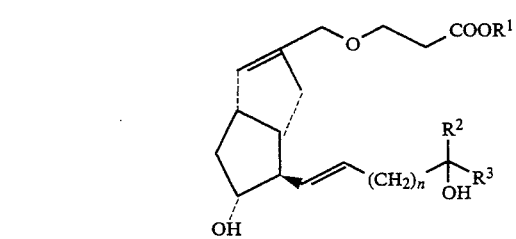

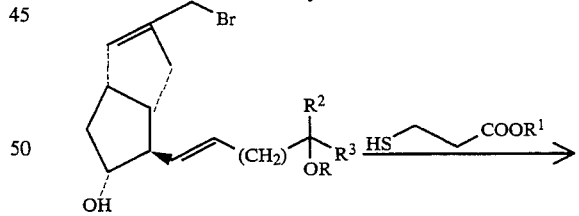

in which R represents a protective group of the hydroxy group

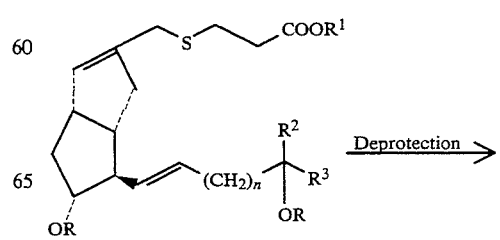

-continued

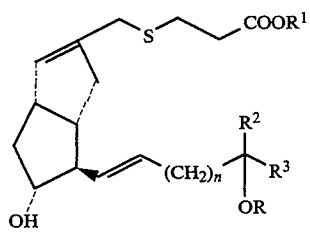

4-thiaisocarbacyclins

Reaction scheme 2

Process for the production of 3-heteroisocarbacyclins

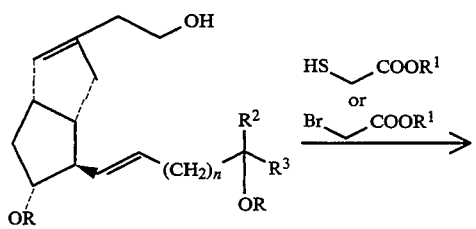

in which R represents a protective group of the hydroxy group.

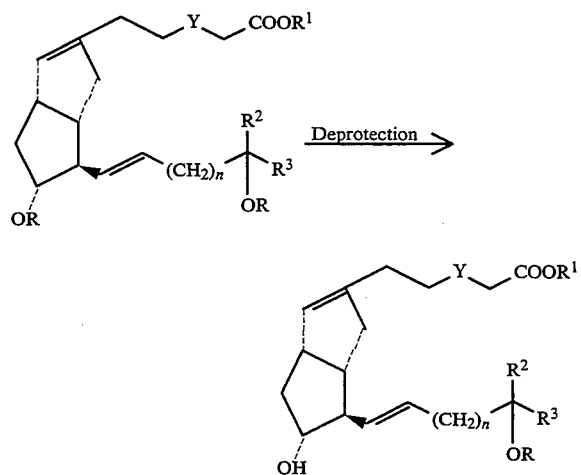

3-heteroisocarbacyclins

Isocarbacyclins of the present invention represented by the above formulae (I+a), (I+b) and (I+c) have a very strong disorder action of organs. For instance, it was clarified by the present invention that these compounds would inhibit the nectrocytosis of hepatocytes induced by carbon tetrachloride or acetoaminophene.

Further, there was confirmed an inhibitory effect of lethal liver nectrocytosis on the autoimmune model mice by the liver antigenic immunity, Among the isocarbacyclins represented by the above formulae (I+a), (I+b) and (I+c) the compound wherein n=0 is generally strong in the circulatory organ action such as antihypertensive action, action to inhibit the platelet aggregation and the like. There is a possibility that this action may be synergistic to display an action of inhibiting the disorder of organs. While, among the isocarbacyclins expressed by the above formula (I) the compound wherein n=1 holds a strong disorder action of organs, whereas the above circulatory organ action is reduced. Thus, the above compound is characterized by being high in the actional selectivity.

The compounds of the present invention can be administered for the therapy or prevention of disorders of organs such as liver, kidney, pancreas, stomach, heart, lung, etc. and diseases caused by cell disorders.

The instantly claimed compounds can be administered to a patient for the therapy or prevention of his or her acute or chronic hepatic diseases such as toxic hepatopathy disorder, adipohepatic, hepatitis (especially, an alcoholic hepatitis and a viral hepatitis), cirrhosis of the liver, fulminant hepatitis, hepatic coma, hepatomegaly, obstruent jaundice, parastic hepatic diseases, hepatic ulcer, hepatic abscess and so on. The claimed compounds can be also employed as a protecting agent of organs in the hepatic preservation at the time of hepatic transplantation. Further, they can be used as a protecting agent of organs for rejection after transplantation.

Moreover, the instantly claimed compounds can be administered for the therapy or prevention of kidney diseases such as nephritis or diabetic nepropathy, pancreatogeneous diseases such as diabetes mellitus or pancreatitis and diseases of organs like stomach, heart or lung. Where using the compounds of the present invention for the above object, they are administered orally or para-orally like intrarectal, subcutaneous, intramuscular, intravaneous, intra-arterial or transepiderminal administration. Suitably, however, it is good to use these compounds depending on the oral or intravaneous administration.

For the purpose of oral administration they can be made into the form of solid or liquid pharmaceutical preparations. As solid pharmaceutical preparations there is a tablet, a pill, a powder or a granule, for example. In such solid pharmaceutical preparations one or more active substances are mixed with at least one pharmaceutically acceptable carrier such as frequently used sodium bicarbonate, calcium carbonate, potato starch, sucrose, mannitol, carboxymethyl cellulose, etc. An operation of making solid pharmaceutical preparations is conducted in the usual way but there may be also contained additives for making into pharmaceutical preparations other than the foregoing, e.g. a lubricant like as calcium stearate, magnesium stearate or glycerine. Further, adjuvants can be contained in the solid pharmaceutical preparations as required.

Liquid pharmaceutical preparations for oral administration contain an emulsion, a solution agent, a suspension, a syrup or a xyl agent, for example. These pharmaceutical preparations contain a commonly used pharmaceutically acceptable carrier, e.g. water or a fluid paraffin.

Oily bases such as coconut oil, graduated coconut oil, soybean oil, corn and the like can be used as a carrier.

Pharmaceutical preparations for oral administration can be manufactured as enteric pharmacueticals having an enteric coating, for example, by spraying an organic solvent or a solution in water of enteric substances such as cellulose acetate phthalate, hydroxypropylmethyl cellulose phthalate, polyvinyl alcohol phthalate, a styrene maleic anhydride copolymer, a methacrylic acid or methyl methacrylate copolymer on the above solid pharmaceutical preparations. Enteric solid pharmaceutical preparations such as powder or granule can be wrapped with a capsule.

Examples of the pharmaceutically acceptable carriers include any other adjuvant, aromatic agent, stabilizer or antiseptic which is usually used as required.

Further, liquid pharmaceutical preparations with powder may be administered by enclosing them in a capsule made of any absorbable substance like gelatine.

Solid pharmaceutical preparations for intrarectal administration contain one or more active substances. There are included suppositories produced in the way known per se.

Pharmaceutical preparations for paraoral administration are provided as a sterile, aqueous or non-aqueous spray, a suspension or an emulsion. The non-aqueous solution or suspension contains propyl glycol, polyethylene glycol or a vegetable oil like olive oil and an injectable organic ester like ethyl oleate as the pharmaceutically acceptable carrier. Such pharmaceutical preparations can also contain an adjuvant such as antiseptic, wetting agent, emulsifier, dispersing agent or stabilizer. These spray, dispersing agent and emulsifier can be made sterile, for example, by conducting the following treatment appropriately, i.e. filtration through a bacteria retention filter, formulation of bactericides or irradiation. Further, sterile solid pharmaceutical preparations can be produced and can be also used by dissolving them in a sterile water or a sterile injection solution immediately before their use.

Further, the instanly claimed compounds can be used by forming an inclusion compound together with alpha- beta or gamma-cyclodextrin or metylated cyclodextrin.

As the dosage form of preparations for transepidermal administration can be given an ointment, a gel cream or the like, for example. They can be molded in the usual way.

Isocarbacyclins of the present invention can be administered to a usual adult in an amount of the order 1 g to 10 mg per day where they are used as a therapeutic agent for disorders of organs in vivo. This daily dosage differs according to the symptomatic degree, age, sex, weight of the patient and dosing route, though. Such dosage can be applied by dividing it into one or several portions per day, e.g. 2 to 6 portions The present invention will be explained in more detail by way of the following referential examples and working examples.

EMBODIMENTS

Referential Example 1

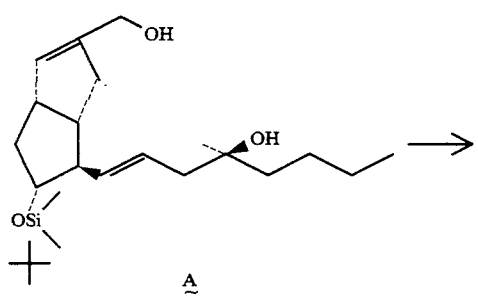

-continued

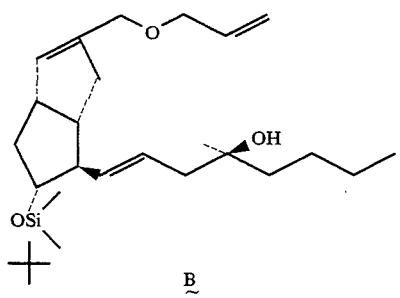

Tetrabutylammonium bisulfate (60 mg, 0.18 mmol) and an aqueous 50% sodium hydroxide solution (3 ml) were added to (16S)-15-deoxy-1,2,3,4-tetranor-5,16-dihydroxy-16-methyl-9(O)-methano-$\Delta^{6(9a)}$-prostaglandin $I_1$ 11-O-t-butyldimethylsilyl ether (compound A; 408 mg, 1.0 mmol) and a solution of allyl bromide (4.41 g, 36 mmol) dissolved in methylene chloride (3 ml) at room temperature, followed by stirring the mixture for 20 hours. After the disappearance of the starting material was confirmed by means of a thin-layer chromatography, an aqueous ammonium chloride solution was added to the reaction solution and its extraction was conducted with ethyl acetate (2×100 ml). The extract was washed with a saturated saline solution and then dried over anhydrous magnesium sulfate. The solvent was evaporated under vacuum and the resultant crude product (529 mg) was purified by means of a silica gel column chromatography (hexane:ethyl acetate=6:1). There resulted an object compound, an allyl ether compound B, (16S)-15-deoxy-1,2,3,4-tetranor-5-allyloxy-16-hydroxy-16-methyl-9(O)-methano-$\Delta^{6(9)}$-prostaglandin $I_1$ 11-O-t-butyldimethylsiliyl ether (355 mg, 0.792 mmol, 79%).

NMR (CDCl$_3$); $\gamma$0.06 (6H, s), 0.93 (12H, s and t), 1.18 (3H, s), 1.2–1.6 (8H, m), 1.8–2.8 (7H, m), 2.8–3.2 (1H, m), 3.5–4.3 (5H, m), 5.0–6.2 (6H, m) ppm Referential Example 2

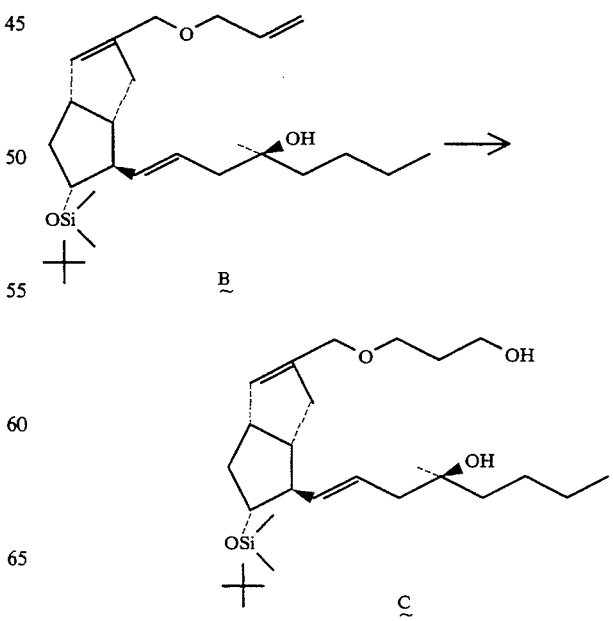

To a solution of compounds B (722 mg, 1.16 mmol) obtained by Referential Example 1 dissolved in tetrahydrofuran (10 ml) was added a solution of 0.5M of 9-borabicyclo[3.3.1]nonane in tetrahydrofuran (10 ml, 5 mmol) at minus 10° C., followed by stirring the mixture at room temperature for 1.5 hours. To the reaction solution were added an aqueous 1N sodium hydroxide solution (10 ml) and 30% hydrogen peroxide (1 ml), followed by stirring the mixture at room temperature for 18 hours. Then ethyl acetate (2×100 ml) was added to the reaction mixture thereby to conduct an extraction. The extract was washed with an aqueous sodium thiosulfate solution and a saline solution in order and was dried over anhydrous magnesium sulfate. The solvent was distilled off under vacuum and the resultant crude product (1.41 g) was purified by subjecting it to a silica gel column chromatography (hexane:ethyl acetate=7:3). There resulted an alcoholic compound C, (16S)-15-deoxy-1,2,3,4-tetranor-5-(3-hydroypropyloxy)-16-hydroxy-16-methyl-9(O)-methano-$\Delta^{6(9\alpha)}$-prostaglandin $I_1$ 11-O-t-butyldimethylsilyl ether (568 mg, 1.22 mmol, 76%).

NMR (CDCl$_{13}$); $\gamma$0.06 (6H, S), 0.93 (12H, s and m), 1.13 (3H, s), 1.2–1.5 (8H, m), 1.5–2.7 (10H, m), 2.7–3.2 (1H, m), 3.4–4.2 (7H, m), 5.2–5.7 (3H, m) ppm IR (neat); 3400, 3050, 2950, 2880, 1460, 1360, 1255, 1115, 975, 910, 860, 840, 780 cm$^{-1}$.

Referential Example 3

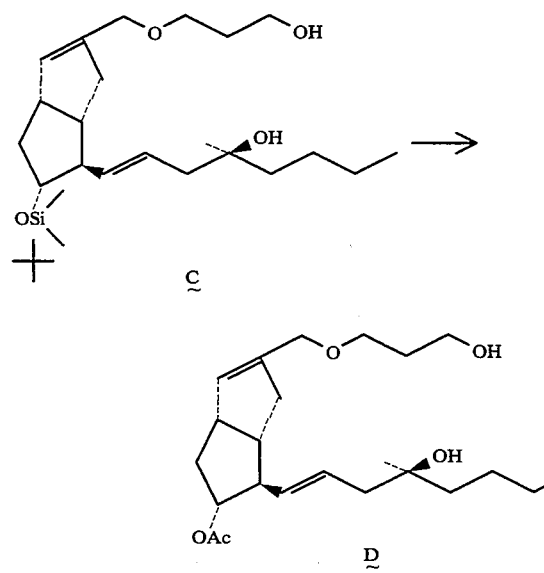

To a solution of compound C (461 mg, 0.99 mmol) obtained by Referential Example 2 dissolved in methylene chloride (10 ml) were added pyridine (5 ml), 4-dimethylaminopyridine (122 mg, 1.0 mmol) and triphenylmethyl chloride (836 mg, 3.0 mmol) at room temperature in sequence, followed by stirring the mixture for 24 hours. After the completion of the reaction, ethyl acetate (3×100 ml) and an aqueous solution of saturated potassium hydrogensulfate were added thereby to conduct an extraction. The extract was washed with a sodium hydrogen-carbonate water and a saline solution in order and was dried over anhydrous magnesium sulfate. Then the solvent was distilled off under vacuum thereby to afford 1.35 g of a crude tritylated product.

This product was dissolved in tetrahydrofuran (10 ml). To the mixture was added a solution of 1.0M tetrabutylammonium fluoride dissolved in tetrahydrofuran (5 ml, 5 mmol), followed by stirring the mixture at room temperature for 18 hours. After the completion of the reaction the solvent was concentrated under vacuum thereby to give a crude tritylated diol. To this was added an acetic anhydride (3 ml) and pyridine (3 ml) and the mixture was stirred at room temperature for 20 hours thereby to acetylate it. After the completion of the reaction ethanol (3 ml) was added to the reaction mixture, followed by stirring the mixture for 30 minutes. Then toluene (3×50 mol) was added to the mixture thereby to conduct an azeotropic distillation. There resulted 2.83 g of a crude tritylated acetate product.

This product was dissolved in methanol (20 ml). To the mixture was added a 1N hydrochloric acid (2 ml). The mixture was stirred at room temperature for 24 hours thereby to conduct its detritylation. An aqueous sodium hydrogencarbonate solution was added to the reaction liquid and then methanol was distilled off under vacuum. The so obtained reaction mixture was extracted with ethyl acetate (3×100 ml). The extract was washed with a saline solution and was dried over anhydrous magnesium sulfate. The solvent was concentrated under vacuum thereby to afford 1.345 g of a crude product. This crude product was separated by subjecting it to a silica gel column chromatography (hexane:ethyl acetate=1:1). There resulted an object compound, a diol acetate compound D, (16S)-15-deoxy-1,2,3,4-tetranor-5,16-dihydroxy-16-methyl-11-O-acetyl-9-(O) methano-$\Delta^{6(9)}$-prostaglandin $I_1$ (309 mg, 0.78 mmol) through a total of four steps and in a total yield of 79%.

NMR (CDCl$_3$); $\gamma$0.93 (3H, t), 1.15 (3H, s), 1.20–1.60 (8H, m), 1.7–2.7 (10H, m), 2.00 (3H, s), 2.9–3.3 (1H, m), 3.5–3.9 (4H, dt), 4.01 (2H, bs), 4.85 (1H, m), 5.3–5.8 (3H, m) ppm. IR (neat); 3440, 3050, 2950, 1740, 1370, 1245, 1150, 1070, 975, 835, 735 cm$^{-1}$.

Referential Example 4

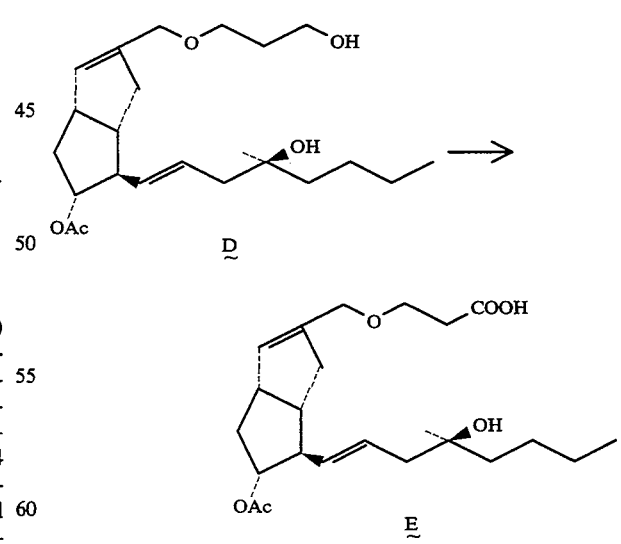

Compound D (271 mg, 0.688 mmol) obtained by Referential Example 3 was dissolved in acetone (16 ml). The Jones' reagent (2 ml) was added to the mixture at 0° C. and its stirring was conducted at room temperature for two hours. To the reaction mixture was added isopropyl alcohol (one mol) thereby to treat an excess oxidizing agent. The extraction was conducted using ethyl acetate (3×100 ml). The extract was washed with a saline solution and was dried over anhydrous magnesium sulfate. The solvent was distilled off under vacuum thereby to afford 259 mg of a crude product. This product was subjected to a silica gel column chromatography (hexane:ethyl acetate=1:4, 0.1% acetic acid). There resulted a carboxylic acid E, (16S)-15-deoxy-11-O-acetyl-16-hydroxy-16-methyl-9-(O)-methano-$\Delta^{6(9\Delta)}$-oxaprostaglandin $I_1$ (132 mg, 0.32 mmol, 47%).

NMR (CDCl$_{13}$); γ0.87 (3H, t), 1.13 (3H, s), 1.2–1.7 (6H, m), 1.96 (3H, s), 2.02–2.8 (10H, m), 2.8–3.3 (1H, m), 3.5–3.8 (2H, m), 2.01 (2H, bs), 4.85 (1H, m), 3.3–3.8 (3H, m), 6.85 (2H, bs) ppm.

Referential Example 5

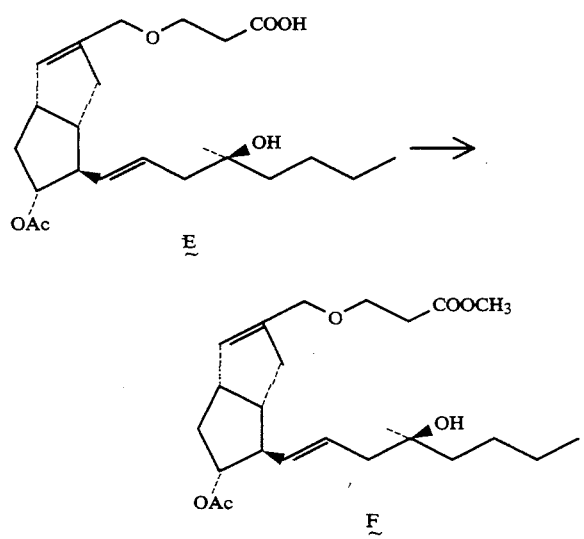

Carboxylic acid E (132 rag, 0.32 mmol) obtained by Referential Example 4 was dissolved in pether (5 ml). A solution of diazomethane dissolved in ether was added to the mixture at 0° C. and its stirring was conducted for 30 minutes. After the disappearance of the starting carboxylic acid was confirmed by means of a thin-layer chromatography, a small amount of acetic acid was added to the reaction liquid thereby to decompose excess diazomethane. The solvent was distilled off under vacuum. The resultant crude product was subjected to a silica gel column chromatography (hexane:ethyl acetate=1:2). There resulted methyl ester F (122 mg, 0.288 mmol, 90%), an object compound.

NMR (CDCl$_{13}$); δ0.90 (3H, t), 1.13 (3H, s), 1.1–1.6 (6H, m), 1.98 (3H, s), 2.1–2.7 (11H, m), 2.8–3.2 (1H, m), 3.5–3.9 (2H, m), 3.78 (3H, s), 4.01 (2H, bs), 4.7–4.9 (1H, m), 5.4–5.7 (3H, m) ppm.

Referential Example 6

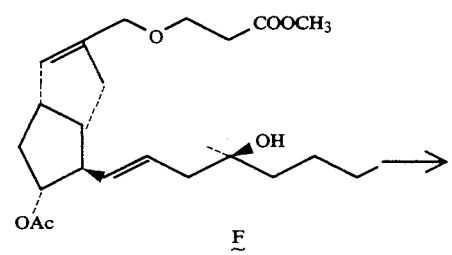

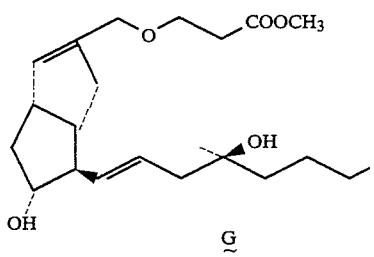

Methyl ester F (122 mg, 0,288 mmol) obtained by Referential Example 5 was dissolved in methanol (8 ml). Five drops of 28% sodium methylate was added to the mixture and its stirring was conducted at room temperature for 6 hours. After the disappearance of the starting material was confirmed by means of a thin-layer chromatography, an aqueous ammonium chloride solution was added to the reaction product thereby to conduct the extraction with ethyl acetate (3×100 ml) and the extract was washed with a saline solution. The resultant organic layer was concentrated thereby to afford 223 mg of a crude product. The resultant product was subjected to a silica gel chromatograrphy (hexane:ethyl acetate=1:3). There resulted an object compound, (16S)-15-deoxy-16-hydroxy-16-methyl-9-(O)-methano-$\Delta^{6(9\alpha)}$-oxaprostaglandin $I_1$ methyl ester G (79 mg, 0,208 mmol, 72%).

NMR (CDCl$_3$); γ0.88 (3H, t), 1.13 (3H, s), 1.1–1.6 (6H, m), 1.7–2.7 (1H, m), 2.8–3.2 (1H, m), 3.5–3.8 (2H, m), 3.67 (3H, s), 3.99 (2H, bs), 5.2–5.8 (3H, m) ppm. IR (neat); 3400, 3050, 2950, 1745, 1440, 1360, 1260, 1200, 1175, 1090, 1075, 1020, 970, 905, 825 cm$^1$. EI-MS; 362 (M-18), 280, 262, 241, 176, 158, 101.

Referential Example 7

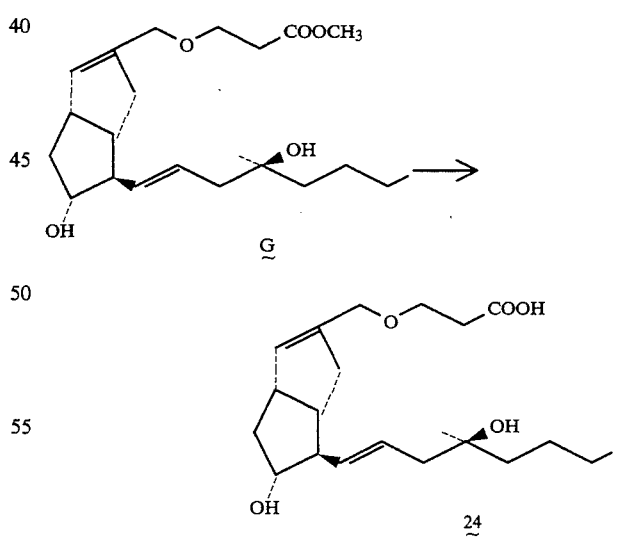

Methyl ester G (79 mg, 0,288 mmol) obtained by Referential Example 6 was dissolved in ethanol (2 ml). An aqueous 5% potassium hydroxide solution was added to the mixture and its stirring was conducted at room temperature for 1.5 hours. A 5N hydrochloric acid was added to the reaction mixture thereby to acidify it. Its extraction was conducted with ethyl acetate (3×100 ml) and the extract was washed with a saline solution. After drying the extract, the solvent was distilled off under vacuum thereby to afford 65 mg of a crude product. This product was purified by subjecting it to a silica gel column chromatography (ethyl acetate). There resulted an object compound, (16S) -15-deoxy-16-hydroxy-16-methyl-9-(O)-methano-$\Delta^{6(9\alpha)}$-4-oxaprostaglandin $I_1$ 24 (62 mg, 0.169 mmol, 81%).

NMR (CDCl$_3$); $\delta$0.93 (3H, t), 1.16 (3H, s), 1.1–1.6 (6H, m), 1.7–2.7 (10H, m), 2.7–3.2 (1H, m), 3.35–4.2 (3H, m), 4.01 (2H, bs), 4.9–5.9 (6H, m) ppm. IR (neat); 3400, 3050, 2950, 1720, 1380, 1260, 1195, 1150, 1090, 1070, 975, 900, 830 cm$^{-1}$. EI-MS; 348 (M-18), 330, 304, 291, 248, 176, 158, 143, 132, 117, 101.

Referential Example 8

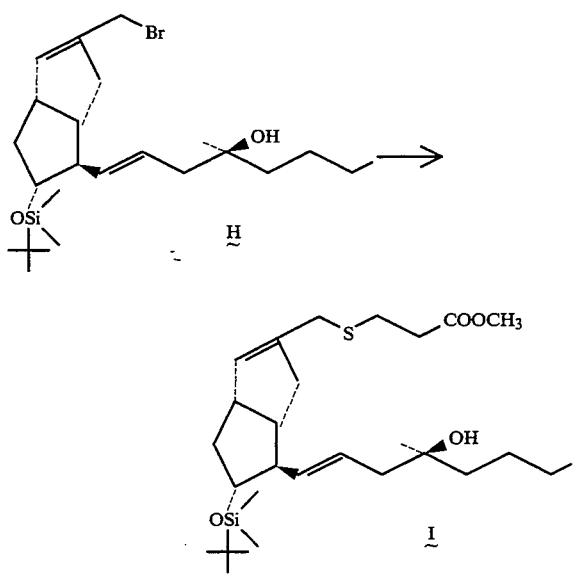

Sodium hydride (content of 60%, 35 mg, 0.88 mmol) was suspended in 1 ml of N,N-dimethylformamide. Then methyl beta-mercapto propionate (106 mg, 0.88 mmol) was added to the suspension and its stirring was conducted at room temperature for 30 minutes. To this reaction solution was added a solution of bromide H, (16S)-15-deoxy-1,2,3,4-tetranor-5-bromo-16-hydrocy-16-methyl-9-(O)-methano-$\Delta^{6(9\alpha)}$-prostaglandin $I_1$ 11-O-t-butyldimethylsilyl ether (138 mg, 0,293 mmol) dissolved in N,N-dimethylformamide (2 ml) and its stirring was conducted at room temperature for 5 hours. After the disappearance of the starting material was confirmed by means of a thin-layer chromatography, an aqueous ammonium chloride solution was added to the reaction mixture thereby to conduct its extraction with ethyl acetate (3×100 ml). The so obtained extract was washed with a saline solution and was dried over anhydrous magnesium sulfate. The solvent was distilled off under vacuum thereby to afford 460 mg of a crude product. This product was subjected to a silica gel column chromatography (hexane:ethyl acetate=6:1). There resulted an object compound I, (16S)-15-deoxy-16-hydroxy-16-methyl-9-(O)- methano-$\Delta^{6(9\alpha)}$-4-thiaprostaglandin $I_1$ methyl ester 11-O-t-butyldimethylsilyl ether (94 mg, 0.184 mmol, 63%).

NMR (CDCl13); $\gamma$0.03 (6H, s), 0.90 (12H, s and t), 1.13 (3H, s), 1.1–1.6 (8H, m), 1.8–3.4 (14H, m), 3.70 (4H, s and m), 5.2–5.8 (3H, m) ppm. IR (neat); 3500, 3050, 2950, 1745, 1460, 1440, 1360, 1250, 1120, 1005, 975, 910, 855, 840, 775, 670 cm$^{-1}$.

Referential Example 9

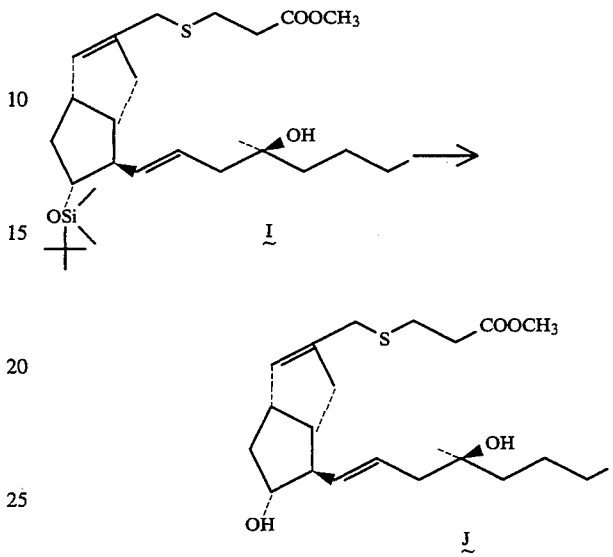

Compound I (94 mg, 0.184 mmol) obtained by Referential Example 8 was dissolved in 3 ml of tetrahydrofuran. To the mixture was added a solution of tetrabutylammonium fluoride dissolved in tetrahydrofuran (1.0 M, 1.0 ml, 1.0 mmol) and its stirring was conducted at room temperature for 5 hours. Then ethyl acetate (3×100 ml) was added to the reaction mixture thereby to conduct its extraction. The resultant extract was washed with an aqueous potassium hydrogensulfate solution and a saline solution in order and was dried over anhydrous magnesium sulfate. Then the solvent was distilled off under vacuum thereby to afford 109 mg of a crude product. This product was purified by subjecting it to a silica gel column chromatography (hexane:ethyl acetate=1:2). There resulted an object compound J, (16S)-15-deoxy-16-hydroxy-16-methyl-9(O)-methano-$\Delta^{6(9\alpha)}$-methano-4-thiaprostaglandin $I_1$ methyl ester (60 mg, 0,118 mmol, 64%).

NMR (CDCl$_3$); $\gamma$0.93 (3H, t), 1.16 (3H, s), 1.1–1.4 (8H, m), 1.7–2.8 (12H, m), 2.8–3.3 (3H, m), 3.55–4.0 (1H, m), 3.68 (3H, s), 5.3–5.8 (3H, m) ppm. IR (neat); 3400, 3050, 2950, 1740, 1440, 1250, 1150, 1090, 970, 905 cm$^{1-}$. EI-MS; 396 (M+), 378, 360,278,158, 101.

Referential Example 10

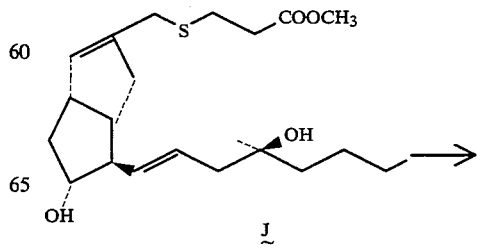

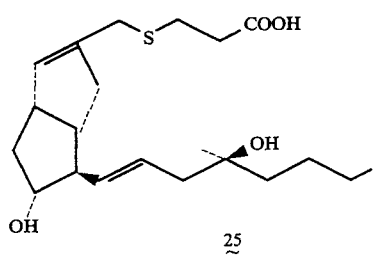

Methyl ester J (30 mg, 0.059 mmol) obtained by Referential Example 9 was dissolved in 1 ml of ethanol. An aqueous 5% potassium hydroxide solution (0.5 ml) was added to the mixture and its stirring was conducted at room temperature for two hours. After acidifing the reaction mixture with a 1N hydrochloric acid, its extraction was conducted with ethyl acetate (3×50 ml). The resultant extract was washed with a saline solution and was dried over anhydrous magnesium sulfate. The solvent was distilled off under vacuum thereby to afford 26 mg of a crude product. This product was purified by means of a silica gel column chromatography (hexane:ethyl acetate=1:9, 0.1% acetic acid). There resulted an object compound 25 (16S)-15-deoxy-16-hydroxy-16-methyl-9-(O)-methano-$\Delta^{6(9\alpha)}$-4-thiaprostaglandin $I_1$ (15 mg, 0.039 mmol, 67%).

NMR (CDCl$_3$); γ0.93 (3H, t), 1.16 (3H, s), 1.1–1.6 (8H, m), 1.7–3.5 (13H, m), 3.6–4.0 (1H, m), 4.55 (3H, bs), 5.2–5.8 (3H, m) ppm. IR (neat); 3400, 3050, 2950, 1720, 1380, 1340, 1260, 1150, 1080, 1030, 970, 900, 800 cm$^{-1}$. EI-MS; 382 (M+), 364, 346, 307, 264, 158, 101.

Referential Example 11

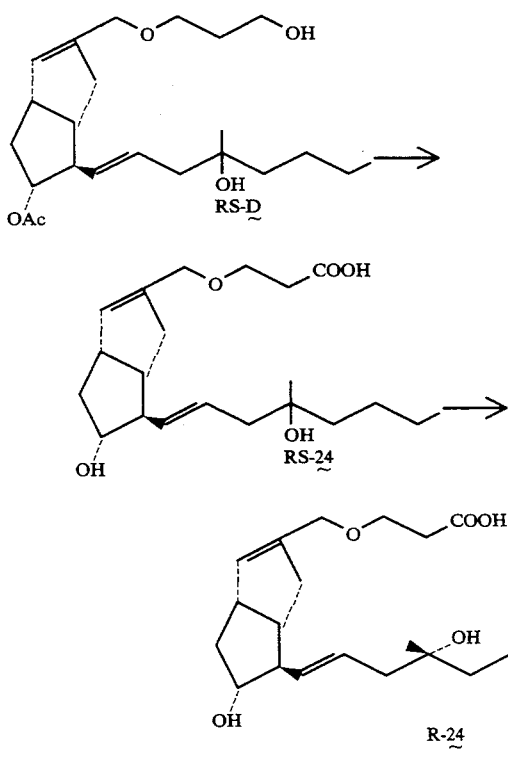

According to the procedure of each of Referential Examples 4 to 7, the following object compound was obtained from compound RS-D i.e. RS-24 (16RS)-15-deoxy-16-hydroxy-16-methyl-9(O)-methano-$\Delta^{6(9\alpha)}$-4-oxaprostaglandin $I_1$. This product was subjected to an HPLC separation (YMC SH-043 S-15 SIL, hexane having an ethanol content of 7.5%, 0.1% acetic acid) thereby to afford (16R)-15-deoxy-16-hydroxy-16-methyl-9(O)-methano-$\Delta^{6(9\alpha)}$-4-oxaprostaglandin I1 R-24

Referential Example 12

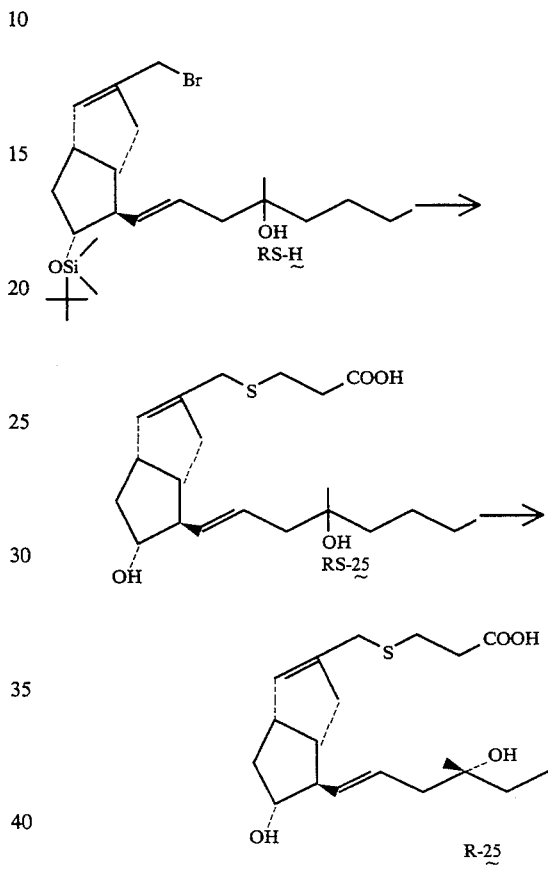

According to the procedure of each of Referential Examples 8 to 10, the following object compound was obtained from compound RS-H, i.e. RS-25, (16R)-15-deoxy-16-hydroxy-16-methyl-9(O)-methano-$\Delta^{6(9\alpha)}$-4-thiaprostaglandin. This product was subjected to an HPLC separation (YMC SH-043 S-151SIL, hexane having an ethanol content of 7.5%, 0.1% acetic acid) thereby to afford (16R)-15-deoxy-16-hydroxy-16-methyl-9(O)-methano-$\Delta^{6(9\alpha)}$-4-thiaprostaglandin $I_1$R-25.

Referential Example 13

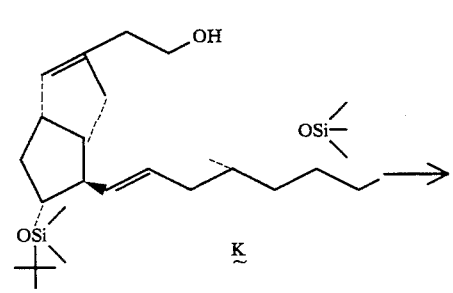

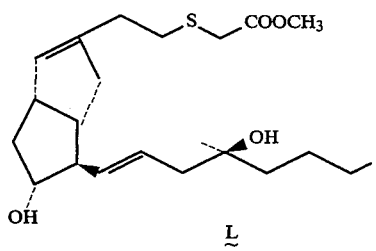

In pyridine (1.2 ml) was dissolved compound K, (16S)-15-deoxy-4,16-dihydroxy-16-methyl-1,2,3-trinor-9-(O)-methano-Δ⁶⁽⁹ᵅ⁾-prostaglandin I₁11-O-t-butyldimethylsilyl 16-trimethylsilyl ether (120.7 mg, 0.214 mmol). To the mixture was added p-toluenesulfonyl chloride (56 mg, 0.3 mmol) and its stirring was conducted at room temperature for 7 hours. After the disappearance of the starting material was confirmed by means of a thin-layer chromatography, ethyl acetate (3×50 ml) was added to the reaction mixture. The resultant organic layer was washed with an aqueous potassium hydrogensulfate solution, an aqueous sodium hydrogencarbonate solution and a saline solution in order and was dried over anhydrous magnesium sulfate. The solvent was distilled off under vacuum thereby to afford 160 mg of a crude tosylate compound.

While, sodium hydride (content of 60%, 20 mg, 0.5 mmol) was suspended in 1.2 ml of N,N-dimethylformamide. Then methylthioglycollic acid (44 mg, 0.5 mmol) was added to the suspension and its stirring was conducted at room temperature for 10 minutes. To this reaction liquid was added a solution of previously prepared tosylate dissolved in N,N-dimethylformamide (3 ml) and its stirring was conducted at room temperature for 15 minutes. After the disappearance of tosylate was confirmed by means of a thin-layer chromatography, an aqueous ammonium chloride solution was added to the reaction product thereby to conduct its extraction with ethyl acetate (3×100 ml). The so obtained extract was washed with a saline solution and was dried over anhydrous magnesium sulfate. The solvent was distilled off under vacuum thereby to afford a crude product, (16S)-15-deoxy-16-trimethylsilyloxy-16-methyl-9-(O)-methano-Δ⁶⁽⁹ᵅ⁾-3-thiaprostaglandin I₁ methyl ester 11-O-t-butyldimethylsilyl ether (506 mg).

A total amount of this product was dissolved in tetrahydrofuran (4 ml). To the mixture was added 1.0M of tetrabutylammonium fluoride (4 ml, 4 mmol) and its stirring was conducted at room temperature for 18 hours. After the completion of the reaction, ethyl acetate (3×50 ml) was added to the reaction mixture and the reaction mixture was washed with an aqueous potassium hydrogensulfate solution, an aqueous sodium hydrogencarbonate solution and a saline solution in order and was dried over anhydrous magnesium sulfate. Then the solvent was distilled off under vacuum thereby to afford 196 mg of a crude product. This product was separated by subjecting it to a silica gel column chromatography (hexane:ethyl acetate=1:2). There resulted an object compound L, (16S)-15-deoxy-16-hydroxy-16-methyl-9(O)-methano-Δ⁶⁽⁹ᵅ⁾-3-thiaprostaglandin I₁ methyl ester, L (56 mg, 0.142 mmol, 56%).

NMR (CDCl₃); γ0.92 (3H, t), 1.16 (3H, s), 1.1–1.6 (8H, m), 1.7–3.1 (13H, m), 3.23 (2H, s), 3.74 (3H, s), 3.6–4.1 (1H, m), 5.2–5.8 (3H, m) ppm. IR (neat); 3400, 3050, 2950, 1740, 1435, 1375, 1280, 1140, 1090, 1010, 975, 905 cm⁻.

Referential Example 14

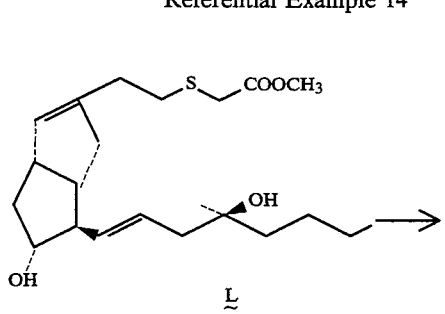

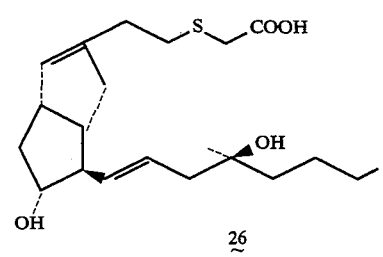

Methyl ester L (40 mg, 0.102 mmol) obtained by Referential Example 13 was dissolved in 2 ml of ethanol. An aqueous 5% potassium hydroxide solution (2 ml) was added to the mixture and its stirring was conducted at room temperature for 1.5 hours. After the completion of the reaction, an aqueous ammonium chloride solution and an aqueous potassium hydrogensulfate solution were added to the reaction mixture thereby to conduct its extraction with ethyl acetate (3×100 ml). The resultant extract was washed with a saline solution and was dried over anhydrous magnesium sulfate. The solvent was distilled off under vacuum thereby to afford an almost pure carboxylic acid 26, (16S)-15-deoxy-16-hydroxy-16-methyl-9-(O)-methano-Δ⁶⁽⁹ᵅ⁾-3-thiaprostaglandin I₁ (38 mg 0.10 mmol, 98% ).

NMR (CDCl₃); γ0.93 (3H, t), 1.17 (3H, s), 1.1–1.7 (8H, m), 1.8–3.2 (11H, m), 3.20 (2H, s), 3.5–4.0 (1H, m), 4.90 (3H, bs), 5.2–5.9 (3H, m) ppm. IR (neat); 3400, 3050, 2950, 2650, 1715, 1380, 1280, 1260, 1140, 1120, 1080, 975, 900 cm⁻¹.

Referential Example 15

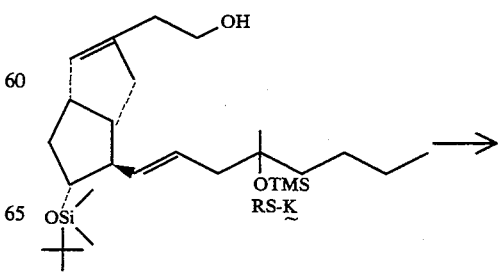

-continued

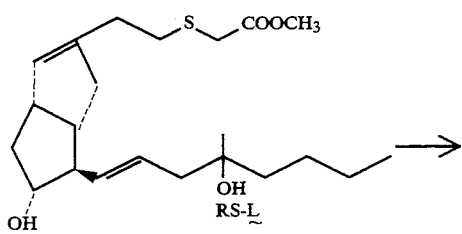

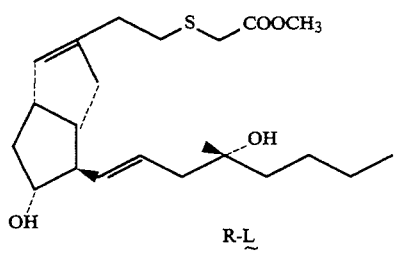

In the same way as that of Referential Example 13, the following compound was obtained from (RS)-alcohol compound, RS-K̰, i.e. diol ester RS-L̰, (16RS)-deoxy-16-deoxy-16-hydroxy-16-methyl-9(O)-methano-$\Delta^{6(9\alpha)}$-3-thiaprostaglandin $I_1$ methyl ester. Its yield was 64%. This product was subjected to a separation depending on the use of a high performance liquid chromatography thereby to afford (16S)-15-deoxy-16-hydroxy-16-methyl-9(O)-methano-$\Delta^{6(9\Delta)}$-3thiaprostaglandin $I_1$ methyl ester R-L̰. Its yield was 41%.

Referential Example 16

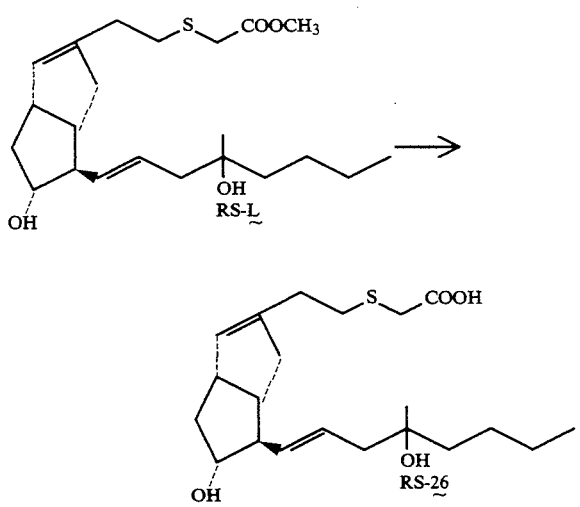

According to the same hydrolysis method as that of Referential Example 14, the following compound was from ester RS-L̰ obtainable by Referential Example 15, i.e. (16RS)-15-deoxy-16-hydroxy-16-methyl-9(O)-methano-$\Delta^{6(9\alpha)}$-thioprostaglandin $I_1$ RS-26̰.

Referential Example 17

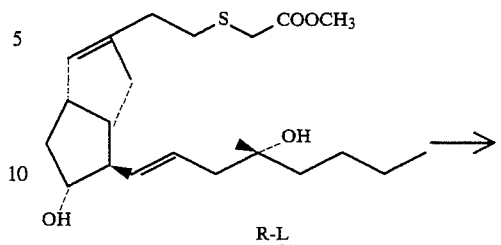

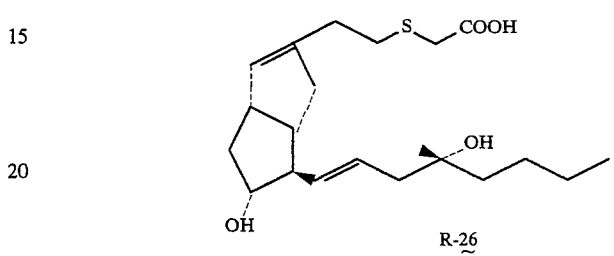

According to the same hydrolysis method as that of Referential Example 14, the following compound was obtained in a yield of 97% from ester R-L̰ obtainable by Referential Example 15, i.e. (16R)-15-deoxy-16-hydroxy-16-methyl-9(O)-methano-$\Delta^{6(9\alpha)}$-3-thiaprostaglandin $I_1$ RS-26̰.

Referential Example 18

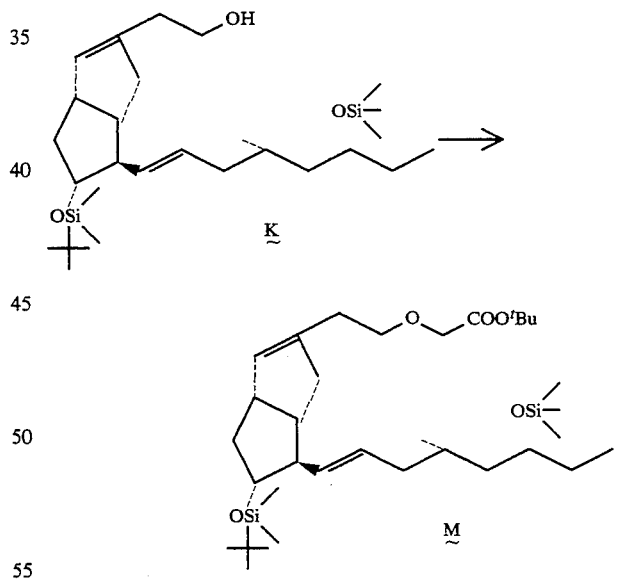

Alcohol compound K̰ (100 mg, 0.20 mmol) used in Referential Example 13 was dissolved in 2 ml of methylene chloride. To the mixture were added bromacetic acid t-butyl ester (1.3 ml, 8 retool), an aqueous 50% potassium hydroxide solution (0.8 ml) and tetrabutylammonium bisulfate (20 mg, 0.06 mmol) in order. Then its stirring was conducted at room temperature for 18 hours. After adding water to the reaction mixture, this was extracted with ether and the separated organic layer was rinsed in an aqueous ammonium chloride solution and a saline solution. After the organic layer was dried over anhydrous magnesium sulfate, this was concentrated thereby to afford a crude product. This was purified by means of a silica gel chromatograpgy (hexane:ethyl acetate=49:). There resulted (16S) -1 5-deoxy-16-trimethylsilyloxy-16-methyl-11-O-t-butlmethylsilyl-9(O)-methano-$\Delta^{6(9\alpha)}$-3-oxaprostaglandin $I_1$ (70 mg, 0,116 mmol, 58%).

NMR (CDCl$_3$); $\gamma$0.06 (6H, t), 0.12 (9H, s), 0.8-1.0 (12H, s+t), 1.17 (3H, s), 1.50 (9H, s), 1.0-2.8 (16H, m), 2.8-3.1 (1H, m), 3.5-3.8 (3H, m), 3.97 (2H, s),ppm, 5.2-5.6 (3H, m) ppm. IR (neat); 2960, 2940, 2860, 1752, 1364, 1246, 1135, 1002, 967, 835, 772 cm$^{-1}$.

Referential Example 19

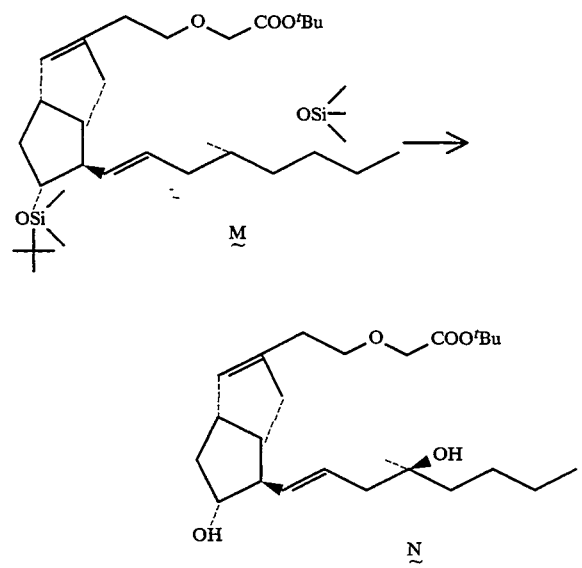

Disilyl ester compound M (472 mg, 0.78 mmol) obtained in Referential Example 18 was dissolved in a solution of 1M tetrabutylammonium fluoride (3.2 ml, 3.2 mmol) dissolved in tetrahydrofuran and its stirring was conducted at room temperature for 13 hours. To the reaction liquid was added an aqueous ammonium chloride solution and its extraction with ether acetate was conducted twice. The separated organic layer was washed with a saline solution and was dried over anhydrous magnesium sulfate. Then this was condensed thereby to afford a crude product. This was subjected to a silica gel chromatograpy thereby to afford (16S)-15-deoxy-16-hydroxy-16-methyl-9-(O)-methano-$\Delta^{6(9\alpha)}$-3-oxaprostaglandin $I_1$t-butyl ester N (311 mg, 0.73 mmol, 94%).

NMR (CDCl$_3$); $\gamma$0.90 (3H, t), 1.15 (3H, s), 1.48 (9H, s), 1.0-2.6 (18H, m), 3.5-3.8 (3H, m), 3.96 (2H, s), 5.2-5.8 (3H, m) ppm. IR (neat); 3400, 2980, 2950, 2900, 1752, 1370, 1230, 1138, 972, 842, 755 cm$^{-1}$. EI-MS; 404 (M-18), 386, 348, 331, 304, 248.

Referential Example 20

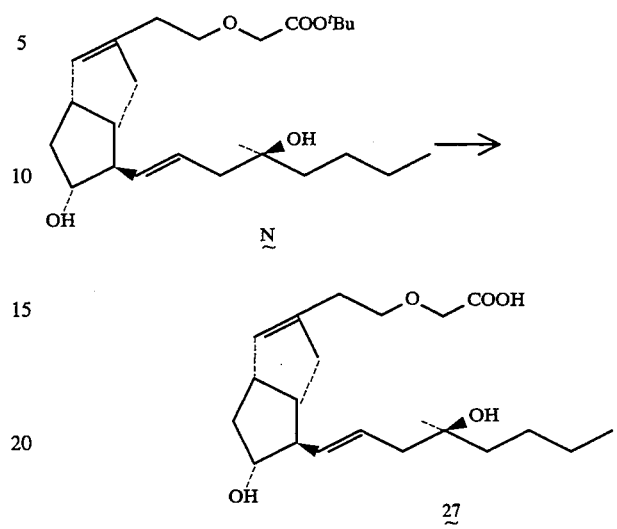

Ester N (214 mg, 0.51 mmol) obtained in Referential Example 19 was dissolved in methanol (3 ml). An aqueous 4N lithium hydroxide solution (0.64 ml, 2.56 mmol) was added to the mixture and its stirring was conducted at room temperature for 14 hours. After adding an aqueous potassium hydrogensulfate solution to the reaction liquid, its extraction with ethyl acetate was conducted. After washing the separated organic layer with a saline solution, this was dried over anhydrous magnesium sulfate. This was concentrated thereby to afford a crude product. This product was subjected to a silica gel chromatograpy (methanol:ethyl acetate=1:19; 0.2% acetic acid) thereby to afford (16S)-15-deoxy-16-hydroxy-16-methyl-9-(O)-methano-$\Delta^{6(9\alpha)}$-3-oxaprostaglandin $I_1$ (172 mg, 0.47 mmol, 92%).

NMR (CDCl$_3$); $\gamma$0.90 (3H, m), 1.16 (3H, s), 1.0-2.6 (16H, m), 2.8-3.2 (1H, bs), 3.4-4.0 (3H, m), 4.08 (2H, s), 5.25 (3H, s), 5.2-5.8 (3H, m) ppm. IR (neat); 3400, 2980, 2950, 2800-2400, 1738, 1135, 1090, 972, 755 cm$^{-1}$.

Example 21

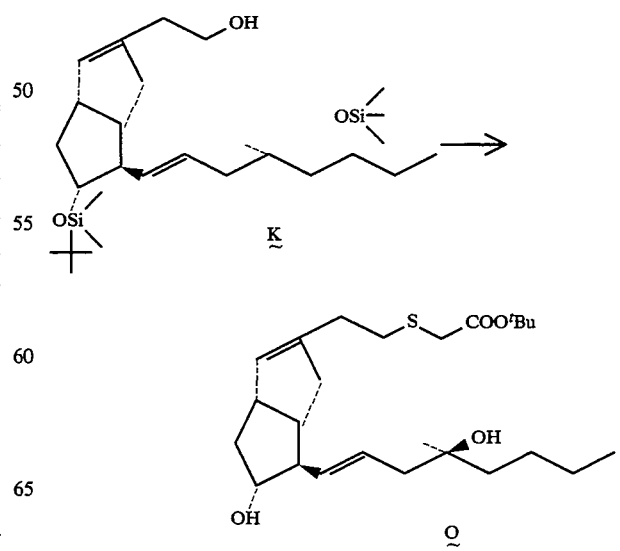

As in Referential Example 13, compound K as the starting material was reacted with thioglycollic acid t-butyl for the formation of sulfide. A crude product obtainable by the same work-up was subjected to desilylation with tetrabutylammonium fluoride in the same way, thereby to afford (16S)-15-deoxy-16-hydroxy-16-methyl-9-(O)-methano-$\Delta^{6(9\alpha)}$-3-thiaprostaglandin $I_1$ t-butyl ester Q (yield of 63%).

NMR (CDCl$_3$); γ0.92 (3H, t), 1.16 (3H, s), 1.47 (9H, s), 1.1–1.6 (8H, m), 1.7–3.1 (13H, s), 3.23 (2H, s), 3.6–4.1 (1H, m), 5.2–5.8 (3H, m) ppm. IR (neat); 3400, 3050, 2950, 1740, 1435, 1375, 1280, 1140, 1090, 1010, 975, 905 cm$^{-1}$.

Referential Example 22

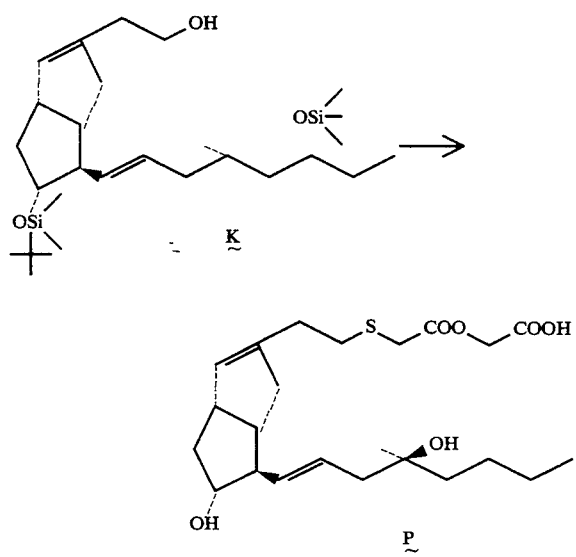

As in Referential Example 13, using compound K as the starting material a hydroxyacetic acid ester of thioglycollic acid was reacted at 0° C. in the presence of two equivalents of sodium hydride. By conducting the successive work-up and desilylation reaction, work-up and purification as in Referential Example 13 there was obtained an object compound P (16S)-15-deoxy-16-hydroxy-16-methyl-9-(O)-methano-$\Delta^{6(9\alpha)}$-3-prostaglandin $I_1$ carboxymethyl ester (yield of 39%).

NMR (CDCl$_3$); γ0.93 (3H, t), 1.17 (3H, s), 1.1–1.7 (8H, m), 1.8–3.2 (11H, m), 3.2 (2H, s), 3.5–4.0 (1-, m), 4.6 (2H, s), 5.2 (3H, bs), 5.2–5.9 (3H, m) ppm. IR (neat); 3400, 3050, 2950, 2650, 1740, 1715, 1380, 1280, 1260, 1140, 1120, 1080, 975, 900 cm$^{-1}$.

Referential Example 23

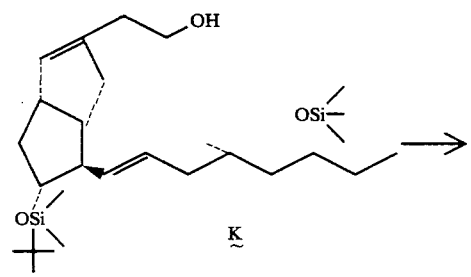

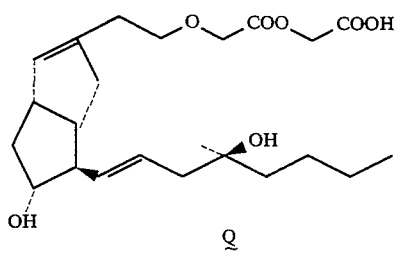

As in Referential Example 18, compound, K as the starting material was reacted with bromoacetic acid hydroxyacetic acid ester and esterified. Then bissilyl ether of the resultant ester was reacted for desilylation as in Referential Example 19. This was purified thereby to afford an object compound. Q, (16S)-15-deoxy-16-hydroxy-16-methyl-9-(O)-methano-$\Delta^{6(9\alpha)}$-3-oxaprostaglandin $I_1$carboxymethyllester. Its total yield was 38%.

NMR (CDCl$_3$); γ0.90 (3H, m), 1.16 (3H, s), 1.0–2.6 (16H, m), 3.4–4.0 (3H, m), 4.10 (2H, s), 4.60 (2H, s), 5.10 (3H, bs), 5.2–5.8 (3H, m) ppm. IR (neat); 3400, 2950, 1740, 1715, 1135, 1090, 970, 755 cm$^{-1}$.

Example 1

Effect on the necrosis of parenchymal liver cells induced by carbon tetrachloride (invivo)

To each of SD type male rats (six week-age; weight of 170–200 g) were administered carbon tetrachloride and a testing medicine in the following procedure. Then the above effect was judged by measuring a glutamic pyruvic acid transaminase (GPT) activity, an index for hepatopathy, in accordance with the ultraviolet portion absorption method (Rate-optimum standard method). Test rats were used in each group of 8 to 36 bodies. The testing medicine was dissolved in a physiological saline solution and administered orally. Every testing medicine was administered five times in total, i.e. 30 minutes before the administration of carbon tetrachloride, 1, 2, 8 and 18 hours after the administration of carbon tetrachloride. Carbon tetrachloride was administered hypodermatically in the form of a 50% olive oil solution at a rate of 0.84 ml/100 g weight (6670 mg/kg weight as carbon tetrachloride). Prior to the administration of carbon tetrachloride, each group of rats was fasted for about 18 hours. Twenty-four hours after the administration of carbon tetrachloride, the rat was etherized and a blood was drawn from its abdominal aorta. Then the blood was allowed to stand at room temperature for one hour and centrifuged at 3000 rpm for 15 minutes. GPT was determined using its supernatant liquid as a serum sample GPT. The result obtained is shown in Table 1. Further, as testing medicines were used (17S)-17,20-dimethyl-9-(O)-methano-$\Delta^{6(9\alpha)}$-prostaglandin $I_1$ [compound (8)] and 15-deoxy-16-hydroxy-16-methyl-9(O)-methano-$\Delta^{6(9\alpha)}$-prostaglandin $I_1$ [compound (21)].

TABLE 1

| Group | GPT (U/ml) | N number |
| --- | --- | --- |
| Intact | 36.6 ± 8.1 | 8 |
| Carbon tetrachloride + vehicle | 3030 ± 1595 | 8 |
| Carbon tetrachloride + compound (8) 1.0 mg/kg | 1682 ± 680 | 8 |
| Carbon tetrachloride + compound (21) 0.3 mg/kg | 1743 ± 592 | 8 |

As is clear from Table 1, the above isocarbacyclins proved to have an inhibitory action of hepatic disorders since they would control a rise of GPT activity involved by carbon tetrachloride.

Example 2

Effect on the necrosis of parenchymal liver cells induced by acetoaminophene (in vivo)

To each ICR type male mouse (five week-age) fasted overnight was administered intracelially 2 mM/kg of acetoaminophene suspended in a 5% acacia. A testing medicine was dissolved in a minimal amount of ethanol. The mixture was diluted with a physiological saline solution and was orally administered to the mouse. Further, the testing medicine was administered three times in total, i.e. 30 minutes before the administration of acetoaminophene, one hour and three hours after its administration. Twenty-four hours after administering acetoaminophene a blood was drawn from the mouse and transaminase (GOT and GPT) activities in the serum were determined. The result obtained is shown in Table 2 below.

Further, as testing medicines were used (17S)-17,20-dimethyl-9-(O)-methano-$\Delta^{6(9\alpha)}$-prostaglandin $I_1$ [compound (8)] and (16S)-15-deoxy-16-hydroxy-16-methyl9-(O)-methano-$\Delta^{6(9\alpha)}$-3-thiaprostaglandin $I_1$[compound (26)].

TABLE 2

| Group | GOT* | GPT* | N number |
| --- | --- | --- | --- |
| Intact | 48 | 19 | 7 |
| Acetoaminophene + vehicle | 4710 | 5240 | 7 |
| Acetoaminophene + compound (8) 1 mg/kg | 1923 | 2726 | 7 |
| Acetoaminophene + compound (26) 1 mg/kg | 1930 | 2250 | 9 |

Note: *indicates Kahmen unit.

As is clear from Table 2, the above isocarbacyclins proved to have an inhibitory action of hepatic disorders since they would control a rise of GOT and GPT activities involved by acetoaminophene.

Example 3

Protective effect of parenchymal liver cells from parenchymal liver cell dyscrasic killer T cells In accordance with the method of M. Ogawa et al. (Liver, vol. 29, No. 12, 1683–1685, 1988) each inbred type 57BL/6 (B6) mouse was immunized with 100,000 g of a supernatant liquid of the liver of the above mouse four times in total a week together with an equivalent amount of Freund's complete adjuvant (FCA). There was prepared an experimental hepatitis model involving any mononuclear cell infiltration and necrosis of parenchymal liver cells centrally in the periportal region. After infecting the mouse with this hepatitis, the sensitized splenoid was obtained from the mouse and was used as an effector cell, while $^{51}Cr$ was taken in the separated parenchymal liver cell from a normal mouse and was employed as a target cell. These target cell and effector cell were mixed at a ratio of 1:100 in the microculture plate and the reaction was conducted for 8 hours under conditions (37° C., 5% $CO_2$). By measuring $^{51}Cr$ liberated from the destructed target cell a study was made about the disorder ability of the effector cell. The result obtained is shown in Table 3.

Further, as the testing medicine was used (16S)-15-deoxy-16-hydroxy-16-methyl-9-(O)-methano-$\Delta^{6(9\alpha)}$-prostaglandin $I_1$ [compound (22)].

TABLE 3

| Kind of the agent | Final concentration | Cell disorder ability (%) |
| --- | --- | --- |
| (—) | | 31.1 ± 4.5* |
| | $10^{-6}M$ | 16.8 ± 2.1* |
| | $10^{-7}$ | 18.4 ± 3.2* |
| Compound (22) | $10^{-8}$ | 21.1 ± 2.6** |
| | $10^{-9}$ | 23.5 ± 3.7*** |
| | $10^{-11}$ | 29.3 ± 1.9 |
| | $10^{-13}$ | 32.5 ± 3.0 |

*$P < 0.001$, $P < 0.005$, *$P < 0.01$

As is clear from Table 3, compound (22) proved to have an inhibitory action of hepatic disorders since they would significantly control a cell disorder ability depending on the experimental system of the present case in a dosage dependent manner.

1) Yoshio Mori et al, Clin. Exp. Immunol., 57:85–92, (1984).
2) Teruo Mori et al, Hepatology, 5:770–777 (1985).

Example 4

Protective effect in the autoimmunizable hepatitis model (in vivo)

In accordance with the method of M. Ogawa et al. (Liver, vol. 28, No. 9, 1226–1232, 1987) a fresh liver obtained from each inbred type 57BL/6 (B6) mouse was homogenized with an equivalent amount of a physiological saline solution. The mixture was centrifuged for one hour thereby to afford 100,000 g of a supernatant liquid. This was used as a hepatic antigen. The line of the backbone of each inbred type mouse was immunized with 0.1 mol of the liver antigen together with an equivalent amount of Freund's complete adjuvant in a range of one to four times. On the seventh day from the final immunization 0.5, 1.0 and 2.0 mg/kg of the testing medicine [compound (22)] was administered by means of single phleboclysis, After the lapse of one hour endotoxicin (ET, 25 μg/mouse; colibacillus LPS026: B6, DIFCO Laboratories, Detroit, Mich. U.S.A.) was dissolved in a physiological saline solution and the mixture was administered to the tail vein. As the control only the physiological saline solution was administered. After its administration, the mouse was observed over a course of 48 hours thereby to calculate the mortality (%). The result obtained is shown in Table 4. Further, the testing medicine [compound (22)] is the same as the compound used in Example 3.

TABLE 4

| | | | mortality |
| --- | --- | --- | --- |
| Group 1 | The group administered with a physiological saline solution + ET | 3/5 | 60% |
| Group 2 | Compound (22) (0.5 mg/kg) + ET | 4/5 | 80% |
| Group 3 | Compound (22) (1.0 mg/kg) + ET | 2/5 | 40% |
| Group 4 | Compound (22) (2.0 mg/kg) + ET | 0/5 | 0% |

As is clear from Table 4, compound (22) also proved to have an inhibitory action of hepatic disorders in the vivo testing since it would control the lethal hepatic necrosis involved by this experimental system in a dosage dependent manner.

Example 5

(Pharmaceutical preparation of ampules) Ampules were produced, each ampule (5 ml) having the following composition:

| Active ingredient | | 200 μg |
|---|---|---|
| Polyethylene glycol 600 | | 200 mg |
| Distilled water | total amount | 50 ml |

Namely, polyethylene glycol and an active ingredient were dissolved in water in the presence of nitrogen. The mixture was boiled, cooled in the presence of nitrogen and distilled. A pre-treated water was added to this solution to bring its volume to a given one and the mixturen was filtered under sterile conditions. Its production is carried out in a diffused light.

The filling operation was conducted in an air flow of nitrogen and the disinfection was performed at 121 °C. for 20 minutes.

As the above active ingredient were used typically (17S)-17,20-dimethyl-9-(O)-methano-$\Delta^{6(9\alpha)}$-prostaglandin $I_1$ [compound (8)], 15-deoxy-16-hydroxy-16-methyl-9(O)-methano-$\Delta^{6(9\alpha)}$-prostaglandin $I_1$ [compound (21)] and its (16S)-compound [compound (22)], and (16S)-15-deoxy-16-hydroxy-16-methyl-9(O)-methano-$\Delta^{(9\alpha)}$-3-thiaprostaglandin $I_1$ [compound (26)].

Example 6

Tablets were produced, each tablet having the following composition:

| Active ingredient | | 20 μg or 100 μg |
|---|---|---|
| Lactose | | 280 mg |
| Potato starch | | 80 mg |
| Polyvinyl pyrrolidone | | 11 mg |
| Magnesium stearate | | 5 mg |
| | Total: | 376 mg |

Namely, the active ingredient, lactose and potato starch were mixed and the mixture was wetted uniformly with a solution of polyvinyl pyrrolidone dissolved in a 20% ethanol uniformly. This was passed through a 20 mm-mesh filter, dried at 45° C. and passed again through a 15 mm-mesh filter. The so obtained granule was mingled in magnesium stearate and the mixture was compressed into the form of a tablet.

As the above active ingredient were used typically (17S)-17,20-dimethyl-9-(O)-methano-$\Delta^{6(9\alpha)}$-prostaglandin $I_1$ [compound (8)], 15-deoxy-16-hydroxy-16-methyl-9(O)-methano-$\Delta^{6(9\alpha)}$-prostaglandin $I_1$ [compound (21)] and its (16S)-compound [compound (22)], and (16S)-15-deoxy-16-hydroxy-16-methyl-9(O)-methano-$\Delta^{6(9\alpha)}$-3-thiaprostaglandin $I_1$ [compound (26)].

Example 7

Hard gelatine capsules were produced, each capsule having the following composition:

| Active ingredient | 20 μg or 100 μg |
|---|---|
| Microcrystalline cellulose | 195 mg |
| Amorphous silicic acid | 5 mg |
| Total: | 200 mg |

Namely, the finely devided active ingredient, microcrystalline cellulose and unpressed amorphous silicic acid were mixed satisfactorily. The resultant mixture was filled in a hard gelatine capsule.

As the above active ingredient were used typically (17S)-17,20-dimethyl-9-(O)-methano-$\Delta^{6(9\alpha)}$-prostaglandin $I_1$ [compound (8)], 15-deoxy-16-hydroxy-16-methyl-9(O)-methano-$\Delta^{6(9\alpha)}$-prostaglandin $I_1$ [compound (21)] and its (16S)-compound [compound (22)], and (16S)-15-deoxy-16-hydroxy-16-methyl-9(O)-methano-$\Delta^{6(9\alpha)}$-hiaprostaglandin $I_1$ [compound (26)].

Example 8

(17S)-17,20-dimethyl-9-(O)-methano-$\Delta^{6(9\alpha)}$-prostaglandin $I_1$ [compound (8)] was dissolved in a graduated coconut oil. Further, a coating ingredient according to the following recipe was dissolved by warming. Soft capsules were produced in the usual way by using a soft capsule production machine so that one capsule may contain 50 μg of (17S)-17,20-dimethyl-9-(O)-methanol-$\Delta^{6(9\alpha)}$-prostaglandin $I_1$.

| Receipe of the coating | |
|---|---|
| Gelatine | 10 wt. parts |
| Glycerine | 5 wt. parts |
| Sorbitan acid | 0.08 wt. parts |
| Purified water | 14 wt. parts |

Similarly, soft capsules containing 50 μg of compound (21) were produced by using 15-deoxy-16-hydroxy-16-methyl-9-(O)-methano-$\Delta^{6(9\alpha)}$-prostaglandin $I_1$ [compound (21)] and its (16S)-compound [compound (22)], (16S) -15-deoxy-16-hydroxy-16-methyl-9-(O)-methano-$\Delta^{6(9\alpha)}$-hiaprostaglandin $I_1$ [compound (26)].

We claim:

1. A method for the treatment of hepatic or nephritic disease in a patient requiring such treatment which comprises administering orally or para-orally to said patient an effective amount of at least one (16S) isocarbacyclin of the following formula:

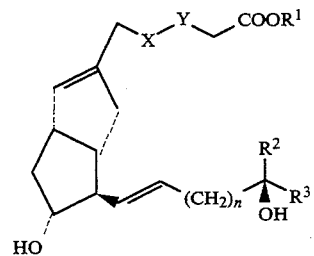

wherein $R^1$ denotes a hydrogen atom, a $C_1$–$C_{10}$ alkyl group, a group —$CH_2COOR^{11}$ in which $R^1$ is a hydrogen atom or a $C_1$–$C_{10}$ alkyl group or one equivalent of cation; $R^2$ denotes a hydrogen atom or a methyl group; $R^3$ denotes a straight chain or branched chain $C_3$–$C_{10}$ alkyl group, a straight chain or branch chain $C_3$–$C_6$ alkyl group substituted by an optionally substituted phenyl group, phenoxy group or a $C_3$–$C_{10}$ cycloalkyl group, a straight chain or branched chain $C_3$–$C_{10}$ alkenyl group, a straight chain or branched chain $C_3$–$C_{10}$ alkynyl group, an optionally substituted $C_3$–$C_{10}$ cycloalkyl group, an optionally substituted phenyl group or an optionally substituted phenoxy group;

n is 1; and substituents for the above optionally substituted groups are a halogen atom, a hydroxyl group, a $C_2$-$C_7$ acyloxy group, a $C_1$-$C_6$ alkyl group optionally substituted by a halogen atom, a $C_1$-$C_4$ alkoxy group optionally substituted by a halogen atom, a nitrile group, a carboxyl group or a $C_1$-$C_6$ alkoxy carbonyl group, and X and Y each is —$CH_2$ or one of X and Y is an oxygen or sulfur atom and the other is —$CH_2$—.

2. A method according to claim 1 wherein $R^2$ denotes a hydrogen atom.

3. A method according to claim 1 wherein $R^3$ denotes a 2-methylhexyl group.

4. A method according to claim 1 wherein $R^2$ denotes a methyl group.

5. A method according to claim 1 wherein $R^3$ denotes an n-butyl group.

6. A method according to claim 1 wherein the isocarbacyclin is (16S)-15-deoxy-16-hydroxy-16-methyl-9-(O)-methano-$\Delta 6^{(9\alpha)}$-prostaglandin $I_1$.

7. A method according to claim 1 wherein $R^1$ denotes a hydrogen atom, a methyl group, a t-butyl group or a carboxylmethyl group.

8. A method according to claim 1 wherein X and Y each is —$CH_2$.

9. A method according to claim 1 wherein X is an oxygen or sulfur atom and Y is —$CH_2$—.

10. A method according to claim 1 wherein X is —$CH_2$— and Y is an oxygen or sulfur atom.

* * * * *